(12) United States Patent
Curro et al.

(10) Patent No.: US 6,452,063 B1
(45) Date of Patent: Sep. 17, 2002

(54) TEAR RESISTANT POROUS EXTENSIBLE WEB

(75) Inventors: John Joseph Curro; Anneka M. Kaminski; Michele Ann Mansfield, all of Cincinnati; George Christopher Dobrin, Mason; Jianbin Zhang, Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/318,046

(22) Filed: May 25, 1999

Related U.S. Application Data

(60) Provisional application No. 60/087,302, filed on May 29, 1998.

(51) Int. Cl.[7] .................................................. A61F 13/15
(52) U.S. Cl. ....................... 604/383; 604/367; 604/370; 604/385.27; 428/73; 428/134; 428/131
(58) Field of Search ................................. 604/358, 365, 604/367, 369, 370, 375, 378, 379, 385.23, 385.22, 385.24, 385.27; 521/57; 428/73, 103, 134, 135, 137, 131

(56) References Cited

U.S. PATENT DOCUMENTS

| | | | | |
|---|---|---|---|---|
| 3,989,867 A | * | 11/1976 | Sisson | ........................ 428/132 |
| 4,324,246 A | * | 4/1982 | Mullane et al. | .............. 128/287 |
| 4,342,314 A | * | 8/1982 | Radel et al. | ................. 128/287 |
| 5,366,782 A | * | 11/1994 | Curro et al. | ................. 428/137 |
| 5,700,255 A | * | 12/1997 | Curro et al. | ............. 604/385.2 |
| 5,804,286 A | * | 9/1998 | Quantrille et al. | ........... 428/198 |
| 5,997,986 A | * | 12/1999 | Turi et al. | ................... 428/138 |
| 6,050,985 A | * | 4/2000 | Lavon et al. | ............. 604/385.2 |

* cited by examiner

Primary Examiner—John G. Weiss
Assistant Examiner—Jacqueline Stephens
(74) Attorney, Agent, or Firm—Ian S. Robinson; Ken K. Patel; Steven W. Miller

(57) ABSTRACT

The present invention pertains to a porous, macroscopically-expanded, three-dimensional, elastomeric web suitable for use in disposable absorbent articles such as bandages, diapers and pull-up diaper training pants, as well as a method for making the web. In a preferred embodiment the web has a continuous first surface and a discontinuous second surface remote front first surface. In a preferred embodiment the elastomeric web exhibits a multiplicity of primary apertures in the first surface of the web, the primary apertures being defined in the plane of the first surface by a continuous network of interconnecting members. Each interconnecting member exhibits an upwardly concave-shaped cross-section along its length. The interconnecting members terminate substantially concurrently with one another to form a secondary aperture in the plane of the second surface of the web.

16 Claims, 15 Drawing Sheets

TEAR RESISTANT POROUS EXTENSIBLE WEB

This application claims benefit of Provisional Appln. 60/087,302 filed May 29, 1998.

FIELD OF THE INVENTION

The present invention relates to porous extensible polymeric webs. In particular, the present invention relates to macroscopically-expanded three-dimensional apertured polymeric webs.

BACKGROUND OF THE INVENTION

It has long been known in the field of disposable absorbent articles that it is desirable to construct absorptive devices, such as disposable diapers, sanitary napkins, incontinent briefs, bandages, wound dressings, and the like, with elastic elements to improve the range of size, ease of motion, and sustained fit. It is also well known that it is preferable, especially in such products intended to be worn in hot and humid conditions, to provide adequate porosity to all areas of the article where undue occlusion of the skin may cause sensitized skin or heat rash. Due to the nature of many disposable absorbent articles there is a high potential for skin irritation due to trapping of moisture and other body exudates between the elasticized portion of the article and the skin of the wearer. Elasticized portions of disposable articles are particularly prone to causing skin irritations as they tend to be more conformable to the body, and therefore more likely to occlude areas of the skin, often for long periods of time. Various methods are known in the art for imparting elasticity to polymer films, and various methods are known in the art for imparting porosity to polymer films, but there remains a need for a polymeric film or web that provides for both adequate elasticity and porosity, such as may be adapted for durable, prolonged use in garments, particularly disposable garments.

Disposable diapers and other absorbent articles fitted with elasticized leg cuffs or elasticized waist bands for a more comfortable fit, as well as providing for better leakage control, are known in the art. Often, the elasticity is accomplished with a heat treatment of polymeric materials that results in a desirable shirring or gathering of a portion of the diaper. One such method of treatment is disclosed in U.S. Pat. No. 4,681,580, issued to Reising et al. on Jul. 21, 1987, and hereby incorporated by reference herein.

An improved method for sequentially stretching a "zero strain" stretch laminate web to impart elasticity thereto is disclosed in U.S. Pat. No. 5,143,679 issued to Weber et al. on Sep. 1, 1992 and hereby incorporated herein by reference. Weber '679 teaches the use of a stretch laminate material formed of at least two plies, one of which is stretchable and elastomeric, while the second ply is elongatable, but not necessarily elastomeric. The plies are either intermittently or substantially continuously secured to one another along at least a portion of their coextensive surfaces while in a substantially untensioned ("zero-strain") condition. Weber '679 further discloses an improved method and apparatus for sequentially stretching the "zero-strain" stretch laminate portions of the web during the incremental stretching process to impart elasticity in the direction of stretching without rupturing the laminate web in the process. Further improvements are taught in U.S. Pat. No. 5,156,793 issued to Buell et al. on Oct. 20, 1992 and U.S. Pat. No. 5,167,897 issued to Weber et al. on Dec. 1, 1992, both of which are hereby incorporated by reference herein.

Elasticized polymeric webs may also be produced from elastomeric materials known in the art, and may be laminates of polymeric materials such as disclosed in U.S. Pat. No. 5,501,679, issued to Krueger et al. on Mar. 26, 1996. Laminates of this type are generally prepared by coextrusion of elastomeric materials and inelastic skin layers followed by stretching the laminate past the elastic limit of the skin layers and then allowing the laminate to recover. Elastomeric webs or films such as those described above may be used in the body hugging portions of garments, such as the waistband portions and leg cuffs, but are generally not porous enough to prevent undesirable skin irritations when used for prolonged periods of time.

Several means of rendering elasticized planar polymer films more porous are known in the art, such as die punching, slitting, and hot-pin melt aperturing. However, when any of the above techniques is applied to thermoplastic elastomeric films, the increase in porosity is accompanied by a decrease in the degree of reliable elastic performance. For example, in the case of circular apertures in a planar film, it is well known that for an applied stress $S_1$, a resultant local stress, $S_2$, is created orthogonal to the applied stress about the apertures. This local stress, $S_2$, is greater than $S_1$, approaching a magnitude up to 3 times the applied stress. For non-round apertures the concentration of stress can be even greater. As a result, apertures become sources of tear initiation sites at their edges, because the edges of the material form the edges of the apertures in the plane of applied stress. For common thermoplastic elastic films, such apertures facilitate tear initiation which can propagate over time leading to catastrophic failure of the film. When used in elasticized portions of disposable absorbent articles, this failure results in the loss of important elastic characteristics, including loss of comfort, fit and use of the absorbent article.

Prior art web structures that do provide adequate porosity so as to be preferable for use as the wearer-contacting surface on disposable absorbent articles have been of two basic varieties, i.e., inherently fluid-pervious structures, such as fibrous nonwovens, and fluid-impervious materials such as polymeric webs which have been provided with a degree of fluid permeability via aperturing to permit fluid and moisture flow therethrough. Neither variety is characteristically elastic, and as a result both are generally used in regions of an absorbent article requiring fluid permeability but not extensibility, such as the body-contacting layer of a catamenial pad.

Commonly assigned U.S. Pat. No. 3,929,135 issued to Thompson on Dec. 30, 1975, and hereby incorporated herein by reference, suggests a suitable body-contacting porous polymeric web for disposable articles. Thompson teaches a macroscopically-expanded, three-dimensional topsheet comprised of liquid-impermeable polymeric material. However, the polymeric material is formed to comprise tapered capillaries, the capillaries having a base opening in the plane of the topsheet, and an apex opening in intimate contact with the absorbent pad utilized in the disposable absorbent bandage. The polymer material taught by Thompson is not generally an elastomer, however, and Thompson depends on the inelastic properties of the heat-molded single layer film to produce the desired three-dimensional structure.

Still another material which has been utilized as a body contacting surface in a disposable absorbent article context is disclosed in commonly assigned U.S. Pat. No. 4,342,314 issued to Radel et al. on Aug. 3, 1982, and hereby incorporated herein by reference. The Radel et al. patent discloses an improved macroscopically-expanded three-dimensional plastic web comprising a regulated continuum of capillary networks originating in and extending from one surface of the web and terminating in the form of apertures in the opposite surface thereof. In a preferred embodiment, the capillary networks are of decreasing size in the direction of liquid transport.

The macroscopically-expanded three-dimensional plastic webs of the type generally described in the aforementioned commonly assigned Thompson and Radel et al. patents have met with good success in permitting adequate liquid permeability due to the porosity provided by the apertures. However, because of material limitations such webs do not generally possess the requisite elasticity to allow the resulting web to have significant elastomeric characteristics. This shortcoming substantially limits the use of such webs in elasticized portions of an absorbent article. Further, when such webs are extended in one or more directions, the open area provided by the apertures, generally reduces. This can significantly reduce the air and moisture permeability of the web which can increase skin irritation, especially when the web is located in a high stretch region of an article, such as a diaper.

Accordingly, it would be desirable to provide a breathable apertured elastomeric web designed to dissociate the effects of an applied strain on the web from the edges of the apertures and hence retard or prevent the onset of tear initiation. More particularly, in a particularly preferred embodiment, it would be desirable to provide a breathable macroscopically-expanded three-dimensional apertured elastomeric web that is able to substantially recover its three-dimensional shape after being subjected to an applied strain of up to about 400% or more. It would also be desirable to provide a breathable macroscopically-expanded three-dimensional apertured web including apertures having a major axis and a minor axis perpendicular to the major axis wherein the major axis is oriented generally orthogonal to the expected direction of elongation of the web during use.

SUMMARY OF THE INVENTION

In a preferred embodiment, the present invention pertains to a macroscopically-expanded, three-dimensional, elastomeric web suitable for use in elasticized portions of disposable absorbent articles such as bandages, diapers and pull-up diaper training pants. In a preferred embodiment the web has a continuous first surface and a discontinuous second surface remote from the first surface. An elastomeric web of the present invention preferably comprises a formed film having at least two polymeric layers, with at least one layer being an elastomer and at least one layer being a substantially less elastomeric skin layer. In a preferred embodiment the elastomeric web exhibits a multiplicity of primary apertures in the first surface of the web, the primary apertures being defined in the plane of the first surface by a continuous network of interconnecting members, each interconnecting member exhibiting an upwardly concave-shaped cross-section along its length. In a preferred embodiment each interconnecting member exhibits a generally U-shaped cross-section along a portion of its length, the cross-section comprising a base portion generally in the plane of the first surface of the web and sidewall portions joined to each edge of the base portion and interconnected with other sidewall portions. The interconnected sidewall portions extend generally in the direction of the second surface of the web, and are interconnected to one another intermediate the first and the second surfaces of the web. The interconnected sidewall portions terminate substantially concurrently with one another to form a secondary aperture in the plane of the second surface of the web.

Also disclosed is a method of producing the elastomeric web of the present invention comprising providing a multilayer elastomeric film, supporting the film on a forming structure, and applying a fluid pressure differential across the thickness of the multilayer film. The fluid pressure differential is sufficiently great to cause the multilayer film to conform to the supporting structure and rupture in at least portions of the formed film.

When used as an extensible, porous member in an absorbent article, the elastomeric layer of the present invention allows the interconnecting members to stretch in the plane of the first surface. The three-dimensional nature of the web places the secondary apertures in a plane of the second surface remote from the plane of the first surface, initially removing web stresses from the tear initiation sites at the edges of the secondary apertures. Initial web strain results in the base of the interconnecting members experiencing strain in the first surface. As the web strain increases, the sidewall portions of the interconnecting members intermediate the first and second surface experience strain as they begin to approach the plane of the first surface. Ultimately, upon adequate web strain, the plane of the second surface approaches the plane of the first surface and the edges of the secondary apertures will experience web strain as well.

Therefore, the three-dimensional nature of the web allows the strain on the interconnecting members in the plane of the first surface to be dissociated from the strain at the secondary apertures in the secondary surface, and therefore decoupled from potential strain-induced stress at tear initiation sites. This dissociation, or decoupling, of the strain-induced stress of the web from strain-induced stress at the secondary apertures significantly increases web reliability by allowing repeated and sustained web strains of up to about 400% or more without failure of the web due to tear initiation at the apertures.

BRIEF DESCRIPTION OF THE DRAWINGS

While the specification concludes with claims particularly pointing out and distinctly claiming the subject matter of the present invention, it is believed that the present invention will be better understood from the following description taken in conjunction with the accompanying drawings in which like reference numerals identify identical elements and wherein:

DETAILED DESCRIPTION OF THE PRESENT INVENTION

Figure 1:
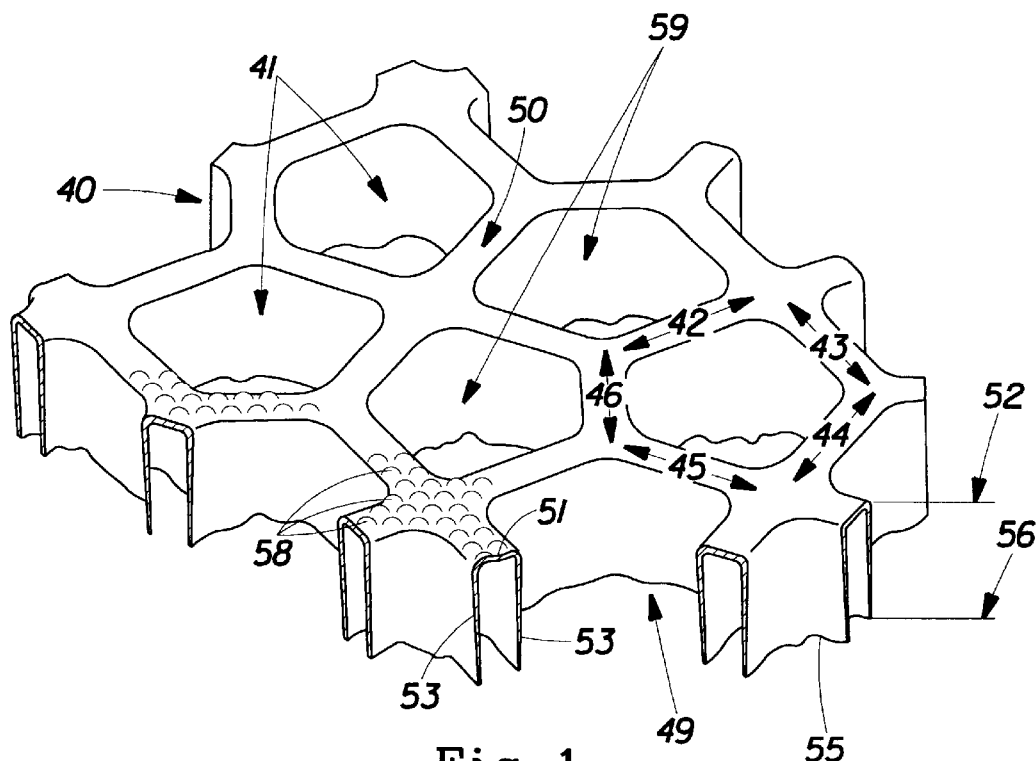
FIG. 1 is an enlarged, partially segmented, perspective illustration of a prior art polymeric web of a type generally disclosed in commonly assigned U.S. Pat. No. 4,342,314.

FIG. 1 is an enlarged, partially segmented, perspective illustration of a prior art macroscopically-expanded, three-dimensional, fiber-like, fluid pervious polymeric web 40 which has been found highly suitable for use as a topsheet in disposable absorbent articles, such as diapers and sanitary napkins. The prior art web is generally in accordance with the teachings of commonly assigned U.S. Pat. No. 4,342,314 issued to Radel et al. on Aug. 3, 1982, which is hereby incorporated herein by reference. The fluid pervious web 40 exhibits a multiplicity of apertures, e.g., apertures 41, which are formed by a multiplicity of interconnected fiber-like elements, e.g., fiber-like elements 42, 43, 44, 45, and 46 interconnected to one another in the first surface 50 of the web. Each fiber-like element comprises a base portion, e.g., base portion 51, located in plane 52 of the first surface 50. Each base portion has a sidewall portion, e.g., sidewall portion 53, attached to each edge thereof. The sidewall portions extend generally in the direction of the second surface 55 of the web. The intersecting sidewall portions of the fiber-like elements are interconnected to one another intermediate the first and second surfaces of the web, and terminate substantially concurrently with one another in the plane 56 of the second surface 55.

In a preferred embodiment, the base portion 51 includes a microscopic pattern of surface aberrations 58 generally in accordance with the teachings of U.S. Pat. No. 4,463,045, issued to Ahr et al. on Jul. 31, 1984, the disclosure of which is hereby incorporated herein by reference. The microscopic pattern of surface aberrations 58 provides a substantially non-glossy visible surface when the web is struck by incident light rays.

In an alternative embodiment the prior web may include a multiplicity of much smaller capillary networks (not shown) in the first surface 50 of the web, as taught by U.S. Pat. No. 4,637,819 to Ouellette et al. issued Jan. 20, 1987 and hereby incorporated herein by reference. It is believed that the additional porosity afforded by the smaller fluid-handling capillary networks may allow the web of the present invention function more efficiently when used as an extensible, porous portion of a disposable absorbent article.

As utilized herein, the term "interconnecting members" refers to some or all of the elements of the elastomeric web, portions of which serve to define the primary apertures by a continuous network. Representative interconnecting members include, but are not limited to, the fiber-like elements of the aforementioned '314 Radel et al. patent and commonly assigned U.S. Pat. No. 5,514,105 to Goodman, Jr., et al. issued on May 7, 1996 and hereby incorporated herein by reference. As can be appreciated from the following description and drawings, the interconnecting elements are inherently continuous, with contiguous interconnecting elements blending into one another in mutually-adjoining transition portions.

Individual interconnecting members can best be generally described, with reference to FIG. 1, as those portions of the elastomeric web disposed between any two adjacent primary apertures, originating in the first surface 50 and extending to the second surface 55. On the first surface of the web the interconnecting members collectively form a continuous network, or pattern, the continuous network of interconnecting members defining the primary apertures, and on the second surface of the web the interconnecting sidewalls of the interconnecting members collectively form a discontinuous pattern of secondary apertures.

As utilized herein, the term "continuous", when used to describe the first surface of the elastomeric web, refers to the uninterrupted character of the first surface, generally in the plane of the first surface. Thus, any point on the first surface can be reached from any and every other point on the first surface without substantially leaving the first surface in the plane of the first surface. Likewise, as utilized herein, the term "discontinuous," when used to describe the second surface of the elastomeric web, refers to the interrupted character of the second surface, generally in the plane of the second surface. Thus, any point on the second surface cannot be reached from every other point on the second surface without substantially leaving the second surface in the plane of the second surface.

In general, as utilized herein the term "macroscopic" is used to refer to structural features or elements which are readily visible to a normal human eye when the perpendicular distance between the viewer's eye and the plane of the web is about 12 inches. Conversely, the term "microscopic" is utilized to refer to structural features or elements which are not readily visible to a normal human eye when the perpendicular distance between the viewer's eye and the plane of the web is about 12 inches.

As utilized herein, the term "macroscopically-expanded", when used to describe three-dimensional elastomeric webs, ribbons and films, refers to elastomeric webs, ribbons and films which have been caused to conform to the surface of a three-dimensional forming structure so that both surfaces thereof exhibit the three-dimensional pattern of the forming structure. Such macroscopically-expanded webs, ribbons and films are typically caused to conform to the surface of the forming structures by embossing (i.e., when the forming structure exhibits a pattern comprised primarily of male projections), by debossing (i.e., when the forming structure exhibits a pattern comprised primarily of female capillary networks), or by extrusion of a resinous melt onto the surface of a forming structure of either type.

By way of contrast, the term "planar" when utilized herein to describe plastic webs, ribbons and films, refers to the overall general condition of the web, ribbon or film when viewed by the naked eye on a macroscopic scale. For example, a non-apertured extruded film or an apertured extruded film that does not exhibit significant macroscopic deformation out of the plane of the film would generally be described as planar. Thus, for an apertured, planar web the edge of the material at the apertures is substantially in the plane of the web, causing applied web stresses in the plane of the web to be coupled directly to tear initiation sites at the apertures.

When macroscopically-expanded, the multilayer film of the elastomeric web of the present invention is formed into three-dimensional interconnecting members which may be described as channel-like. Their two-dimensional cross-section may also be described as "U-shaped", as in the aforementioned Radel et al. patent, or more generally as "upwardly concave-shaped", as disclosed in the aforementioned Goodman, Jr., et al. patent. "Upwardly concave-shaped" as used herein describes the orientation of the channel-like shape with relation to the surfaces of the elastomeric web, with the base generally in the first surface, and the legs of the channel extending from the base in the direction of the second surface, and with the channel opening being substantially in the second surface. In general, as described below with reference to FIG. 5, for a plane extending through the web orthogonal to the plane of the first surface and intersecting any two adjacent primary apertures, the resulting cross-section of an interconnecting member disposed between will exhibit a generally upwardly concave shape that may be substantially U-shaped.

One drawback associated with prior art macroscopically-expanded, three-dimensional, fluid pervious polymeric webs is that despite their superior breathability and fluid handling characteristics, they are not generally elastic enough to be used in the high-stretch portions of disposable absorbent articles, such as waistbands, leg cuffs, and the like. Non-apertured planar elasticized polymeric webs that do exhibit suitable extensibility for use on disposable absorbent articles have drawbacks as well. In particular, non-apertured planar elasticized polymeric webs do not have adequate porosity for use in body-contacting portions of an absorbent article.

Several means of rendering non-apertured planar elasticized polymeric webs more porous are known in the art, such as die punching, slitting, and hot-pin melt aperturing. However, when any of the above techniques is applied to thermoplastic elastomeric films, the increase in porosity is typically accompanied by a decrease in the degree of reliable elastic performance. Once perforated by conventional methods the edges of the apertures become sources of tear initiation sites as forces are applied to the web since they lie in the plane of applied stress. For common thermoplastic elastic films, web stress will initiate tears at the apertures which propagate over time leading to catastrophic failure of the film. If the aperture shapes are non-round, e.g., square, triangular, or other polygons, potential for tear initiation increases due to the stress concentrations at the angular intersection of sides.

Applicant has discovered that if a planar elastomeric web can be formed into a macroscopically-expanded, three-dimensional, fluid pervious web, generally in accordance with the teachings of the aforementioned '314 Radel et al. patent, the resulting three-dimensional elastomeric web exhibits the advantages of high porosity and high elasticity, as well as reliability, and high strength. Applicant has accomplished this in the present invention by utilizing a multilayer polymeric web comprising an elastomeric layer in combination with at least one skin layer, and forming the multilayer web into a macroscopically-expanded, three-dimensional configuration.

As used herein, the term "elastomer" is meant to include any material which is capable of being formed into a film layer and which exhibits elastomeric properties. "Elastomeric" means that the material will substantially resume its original shape after being stretched and, preferably, will sustain only small permanent set following deformation and relaxation. Preferably, the elastomeric layer itself is capable of undergoing from 50% to 1200% elongation at room temperature when in a non-apertured, planar condition. The elastomer can be either pure elastomers or a blend with an elastomeric phase or content that will still exhibit substantial elastomeric properties at ambient temperatures, including human body temperatures.

As used herein, "skin layer" refers to a layer of any semi-crystalline or amorphous polymer that is less elastic than the elastomeric layer. The skin layer of the present invention is preferably thinner and substantially less elastic than the elastomeric layer, and may in the limiting case be generally inelastic. There may be more than one skin layer used in conjunction with the elastomeric layer of the present invention, and it, or they, will generally modify the elastic properties of the elastomer. If more than one skin layer is used, the skin layers may have the same or different material characteristics. Without being bound by theory it is believed that skin layers serve to maintain the three-dimensional structure of the formed elastomeric web of the present invention.

Figure 2:
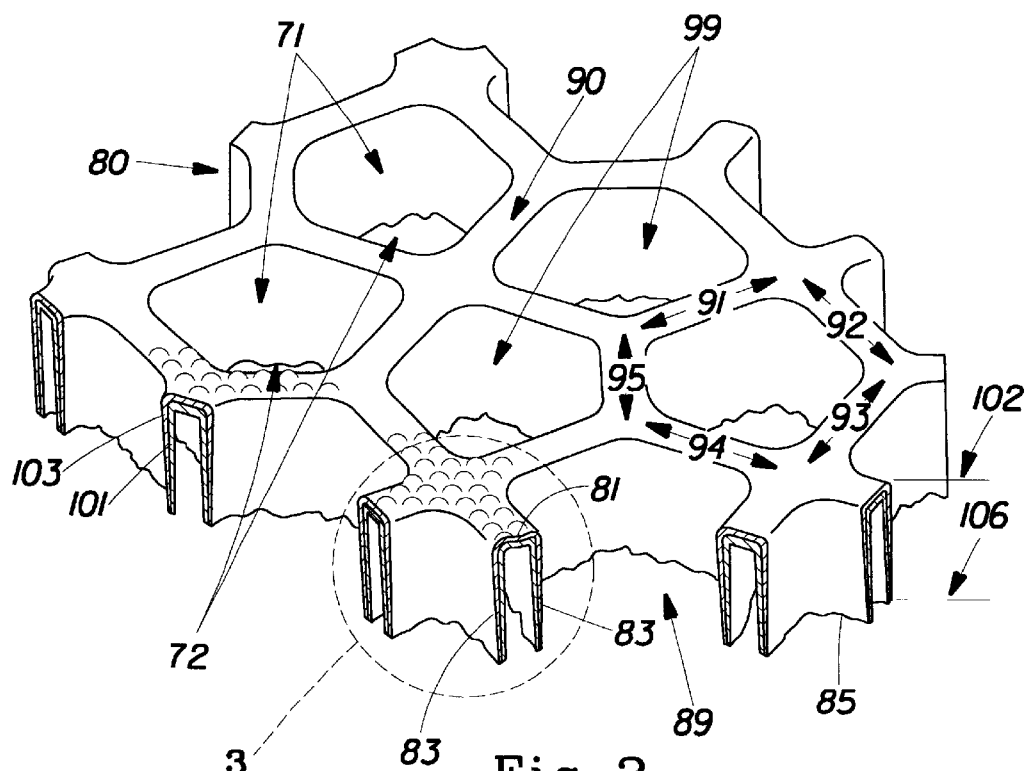
FIG. 2 is an enlarged, partially segmented, perspective illustration of a preferred elastomeric web of the present invention having two layers of polymer film, at least one of which is elastomeric.

FIG. 2 is an enlarged partially segmented, perspective illustration of a macroscopically-expanded, three-dimensional, elastomeric web embodiment of the present invention, generally indicated as 80. The geometrical configuration of the fluid-pervious, elastomeric web 80 is generally similar to that of prior art web 40, illustrated in FIG. 1, and is generally in accordance with the teachings of the aforementioned '314 Radel et al. patent. Other suitable formed film configurations are described in U.S. Pat. No. 3,929,135, issued to Thompson on Dec. 30, 1975; U.S. Pat. No. 4,324,246 issued to Mullane, et al. on Apr. 13, 1982; and U.S. Pat. No. 5,006,394 issued to Baird on Apr. 9, 1991. The disclosures of each of these patents are hereby incorporated herein by reference.

A preferred embodiment of an elastomeric web 80 of the present invention exhibits a multiplicity of primary apertures, e.g., primary apertures 71, which are formed in plane 102 of the first surface 90 by a continuous network of interconnecting members, e.g., members 91, 92, 93, 94, 95 interconnected to one another. The shape of primary apertures 71 as projected on the plane of the first surface 90 are preferably in the shape of polygons, e.g., squares, hexagons, circles, ovals, etc., in an ordered or random pattern. In a preferred embodiment each interconnecting member comprises a base portion, e.g., base portion 81, located in plane 102, and each base portion has a sidewall portion, e.g., sidewall portions 83, attached to each edge thereof. The sidewall portions 83 extend generally in the direction of the second surface 85 of the web and intersect with side walls of adjoining interconnecting members. The intersecting sidewall portions are interconnected to one another intermediate the first and second surfaces of the web, and terminate substantially concurrently with one another to form a secondary aperture, e.g., secondary apertures 72 in the plane 106 of the second surface 85.

Figure 3:
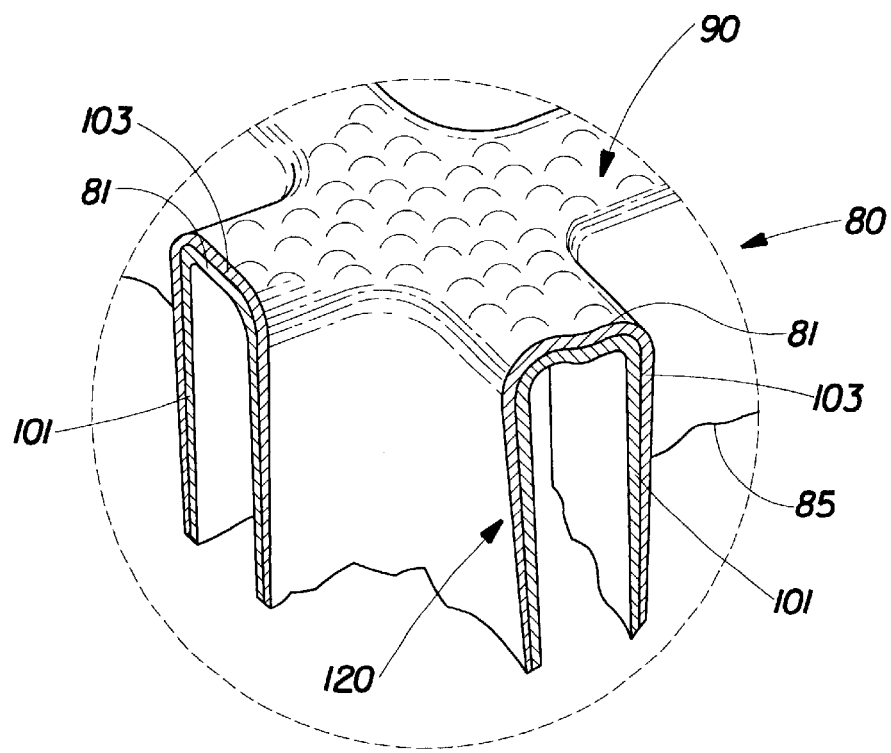
FIG. 3 is a further enlarged, partial view of a web of the type generally shown in FIG. 2, but illustrating in greater detail the web construction of an alternative elastomeric web of the present invention.

FIG. 3 is a further enlarged, partial view of a web of the type generally similar to web 80 of FIG. 2, but illustrating an alternative web construction according to the present invention. The multilayer polymeric formed film 120 of web 80 is preferably comprised of at least one elastomeric layer 101, and at least one skin layer 103. While FIG. 3 shows a two-layer embodiment with the skin layer 103 nearer the first surface 90, it is believed that the order of layering of the formed film 120 is not limiting. While it is presently preferred that as shown in FIG. 3 the polymeric layers terminate substantially concurrently in the plane of the second surface, it is not presently believed to be essential that they do so, i.e., one or more layers may extend further toward the second surface than the others.

Figure 4:
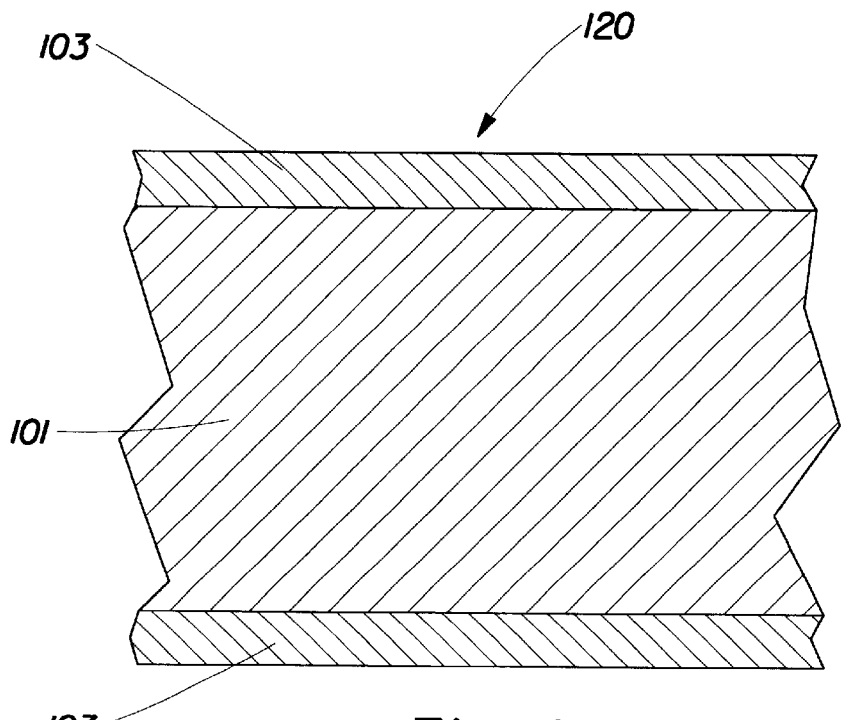
FIG. 4 is an enlarged cross-sectional view of a preferred multilayer film of an elastomeric web of the present invention having an elastomeric layer interposed between two skin layers.

A particularly preferred multilayer polymeric film 120 of the web 80 is depicted in cross-section in FIG. 4, showing an elastomeric layer 101 interposed between two skin layers 103. The elastomeric layer 101 preferably comprises a thermoplastic elastomer comprised of a substantially continuous amorphous matrix, with glassy or crystalline domains interspersed throughout, the domains acting as effective physical crosslinks and hence enabling the material to exhibit an elastic memory when subjected to an applied strain and subsequently released. Preferred elastomeric materials include block copolymers and blends thereof, such as styrene-butadiene-styrene, styrene-isoprene/butadiene-styrene or other such common styrenic block copolymers as are generally available from the Shell Company under the trade name "KRATON", or Kuraray America, Inc. under the trade name "SEPTON". Similarly, polyolefinic materials such as polyethylene and polypropylene generally of densities below about 0.9 g/cc could likewise exhibit the necessary thermoplastic character and resultant elastic behavior. The skin layers preferably comprise any thermoplastic polymer, especially polyolefinic polymers such as polyethylene or polypropylene, generally of density greater than about 0.9 g/cc which are capable of thermoplastic processing into thin films. The skin layer should have sufficient adhesion to the elastomeric layer such that it will not completely delaminate either before or after stretching of the web. A preferred method to produce the multilayer polymeric film 120 is coextrusion.

Figure 5:
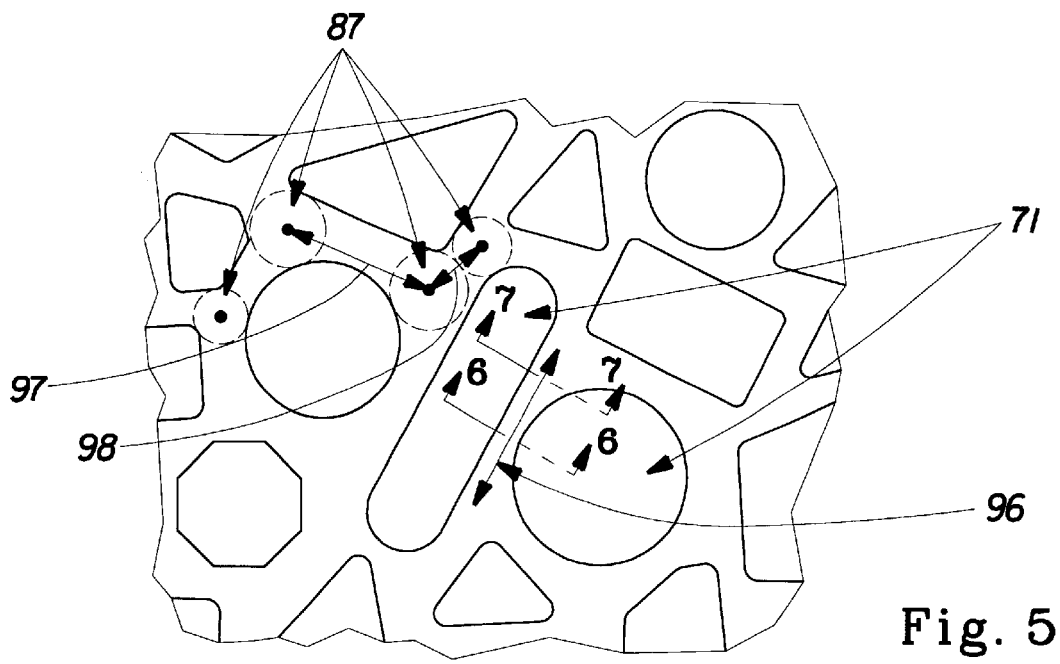
FIG. 5 is a plan view of aperture shapes projected in the plane of the first surface of an alternative elastomeric web of the present invention.
Figure 6:
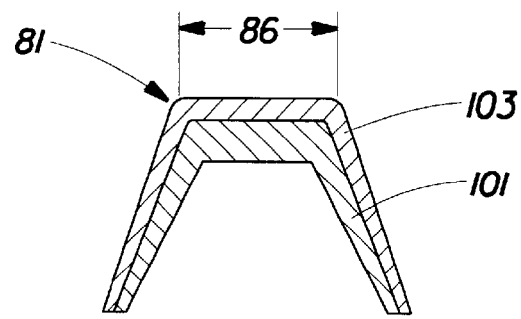
FIG. 6 is an enlarged cross-sectional view of an interconnecting member taken along section line 6—6 of FIG. 5.
Figure 7:
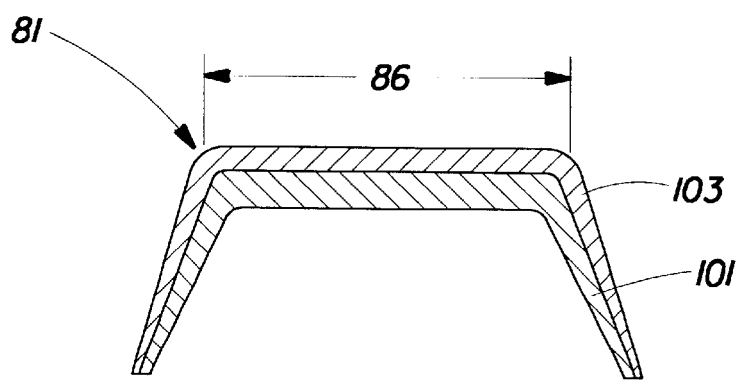
FIG. 7 is another enlarged cross-sectional view of an interconnecting member taken along section line 7—7 of FIG. 5.

FIG. 5 is a plan view of alternative primary aperture shapes projected in the plane of the first surface of an alternative elastomeric web of the present invention. While a repeating pattern of uniform shapes is preferred, the shape of primary apertures, e.g., apertures 71, may be generally circular, polygonal, or mixed, and may be arrayed in an ordered pattern or in a random pattern. It is understood that the projected shape may also be elliptical, tear-drop shaped, or any other shape.

Figure 20:
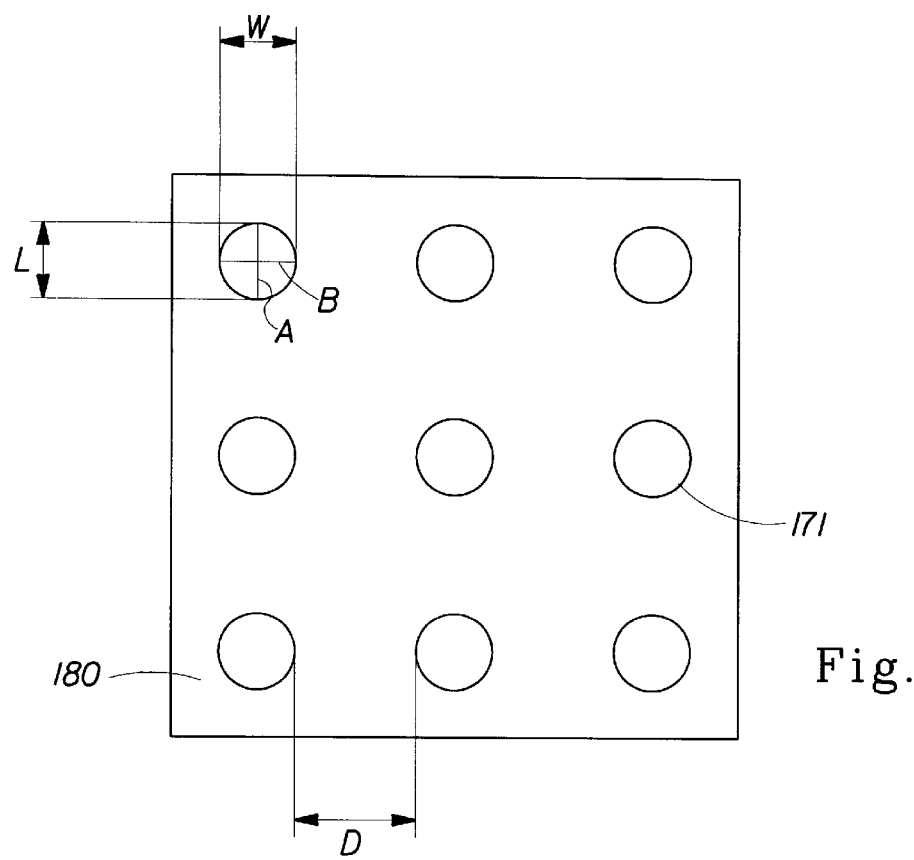
FIG. 20 is an enlarged, partially segmented, plan view of a preferred elastomeric web of the present invention in an untensioned state.
Figure 21:
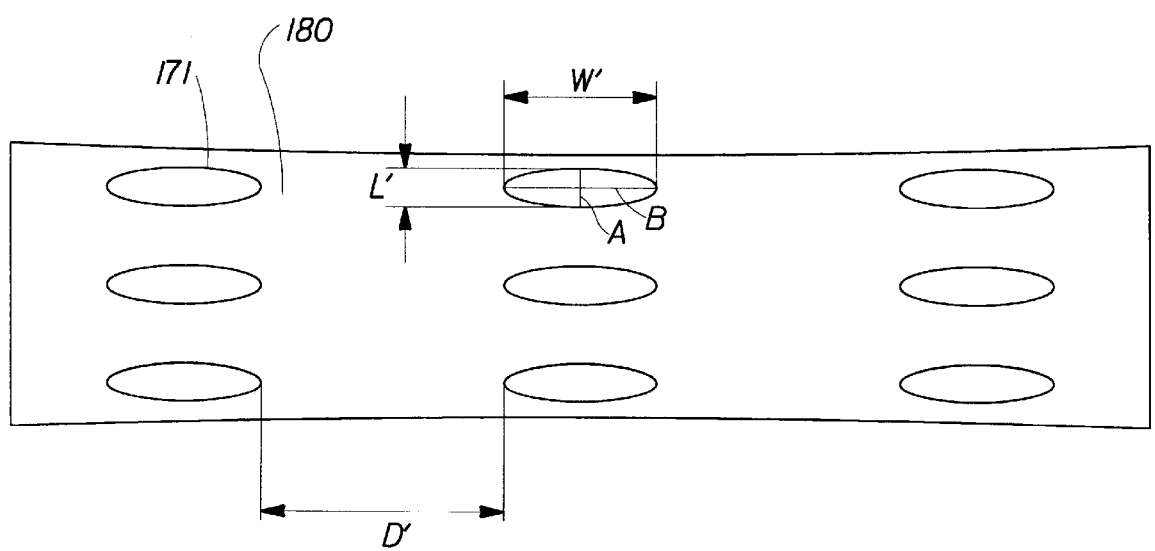
FIG. 21 is an enlarged, partially segmented, plan view of the film of FIG. 20 in an extended state.
Figure 22:
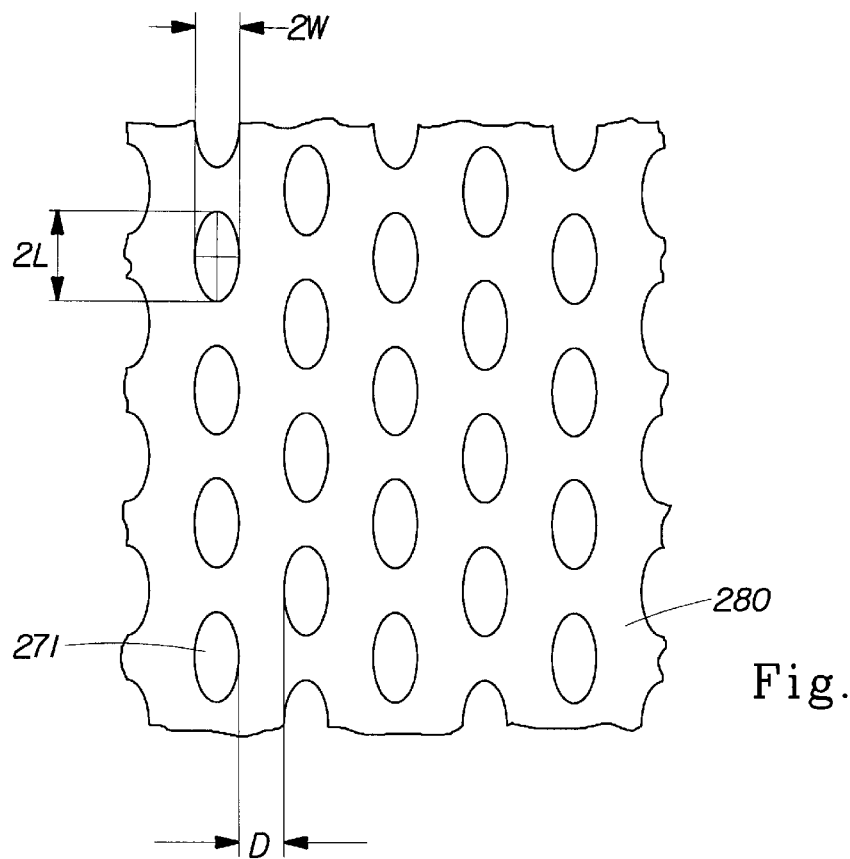
FIG. 22 is an enlarged, partially segmented, plan view of a preferred elastomeric web of the present invention in an untensioned state.

Although the plan view of the primary aperture 71 may be any shape or size, it has been found that the particular geometry of the apertures 71 may provide unexpected benefits related to the air and vapor permeability (i.e., breathability) of the web 80. The unexpected benefits of particular geometry of the apertures 71 are especially evident when the web 80 is extended 50% or more in at least one direction because such extensions can cause the apertures to shrink or substantially close if they are not properly configured. For example, FIGS. 20 and 22 are illustrative examples of embodiments of the elastomeric web 180 of the present invention in an untensioned configuration, each including a plurality of primary apertures 171. The primary apertures 171 of the web 180 in FIG. 20 are generally circular. The apertures 171 have a major axis A and a minor axis B, wherein the length of the major axis A is designated "L" and the length of the minor axis is designated "W". Because other apertures 171 are generally circular, the length L of the major axis A is the same as the length W of the minor axis B when the web 180 is in an untensioned condition. However, when the web 180 is extended, as shown in FIG. 21, the shape of the apertures 171 is changed as well as the distance D between the apertures 171. The length L' of the major axis A is decreased and the length W' of the minor axis B is increased as the web is extended in a direction generally orthogonal to the major axis A. (As used herein, the term "generally orthogonal" refers to an orientation between two axes or directions of about 90°. However, the term also encompassed included angles of between about 45° and about 135°.) As the web 180 is extended further, the plan view area of apertures 171 generally decreases. (As used herein, the "plan view area" of an aperture is the area of an individual aperture when viewed perpendicular to the continuous first surface.) This decrease, in turn, effects a reduction in the percentage open area of the web. (As used herein, the term "percentage open area" for a selected region equals the sum of the plan view area measurements of all the apertures within the selected region divided by the total area of the selected region, expressed as a percentage. Several methods are known in the art to measure percentage open area of porous webs, such as direct light microscope geometric inspection, light projection of the porous web followed by tracing the aperture out lines on the projection screen and cutting and weighing the total aperture cut-out projections and dividing by the total projected area weight. A preferred method used here utilizes light microscopy and video-computer analysis using Optimus 1A software. The aperture area was calibrated by setting a threshold gray-scale value for the aperture area and ratioing this total aperture area to the rest of area in the image.) Further, because the distance D' between the apertures 171 is greater than the percentage open area of the web 181 is significantly reduced. The open area measurements of a web similar to those shown in FIG. 20 (untensioned) and 21 (tensioned) are tabulated in Table I, below.

Figure 23:
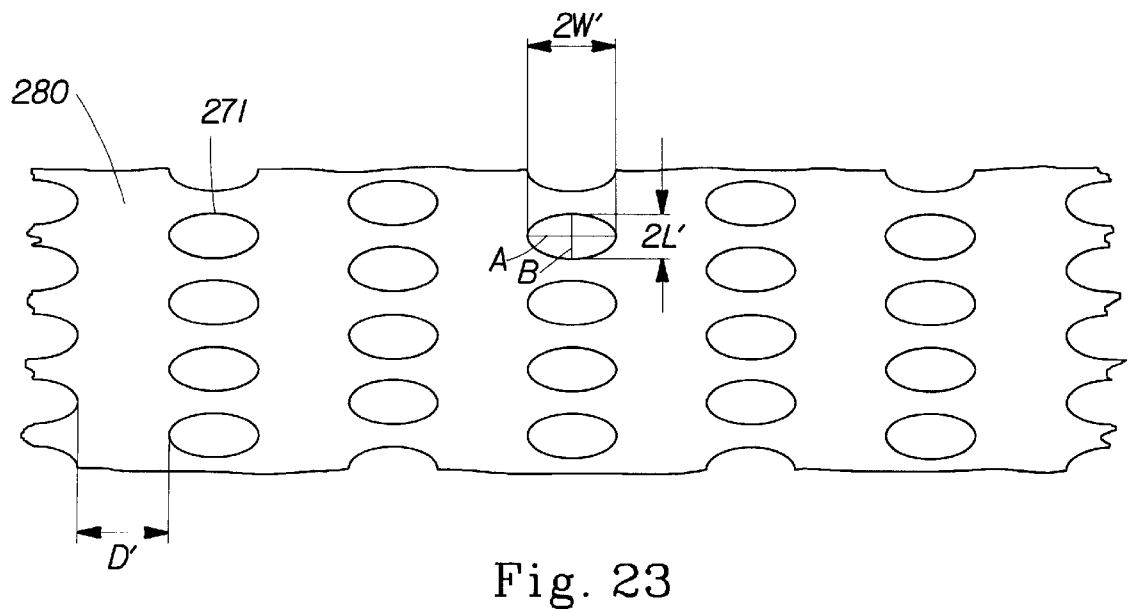
FIG. 23 is an enlarged, partially segmented, plan view of the film of FIG. 20 in an extended state.
Figure 24:
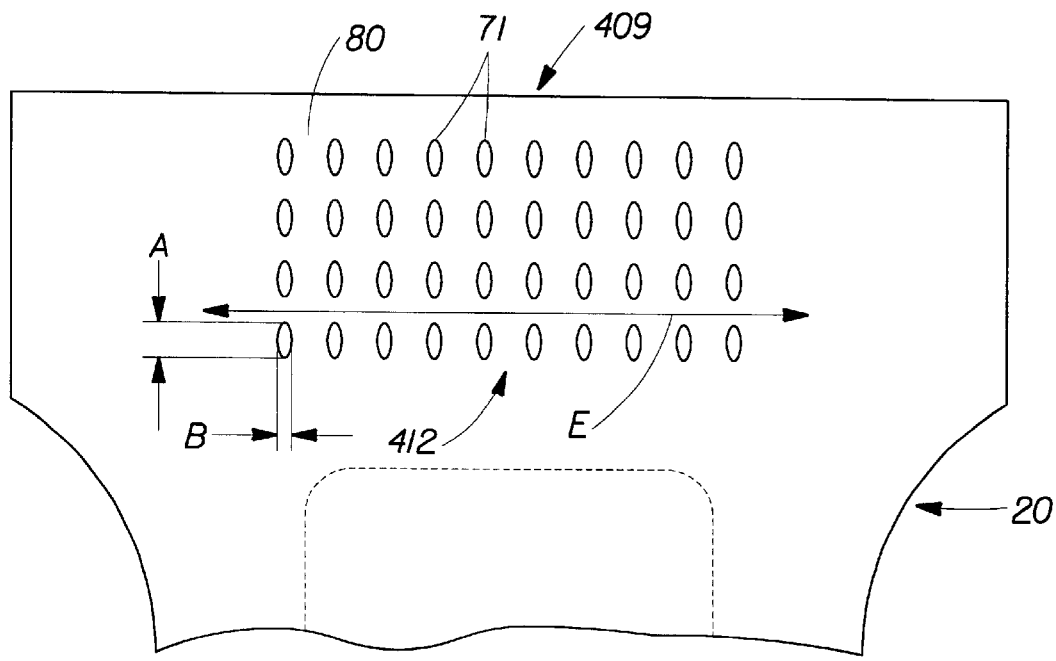
FIG. 24 is a simplified, partially segmented illustration of a waistband for a disposable article.

FIGS. 22 and 23 illustrate a preferred embodiment of the present invention wherein the web 280 includes a plurality of primary apertures 271 which are generally elliptical. Each primary aperture 271 has a major axis A and a minor axis B perpendicular to the major axis A. As shown in FIG. 22, when in an untensioned state, the length 2L of the major axis A is longer than the length 2W of the minor axis B. In a preferred embodiment, the aspect ratio (length of major axis A:length of primary axis B) is greater than about 1.5:1. More preferably, the aspect ratio is greater than about 2:1, and can be about 3:1, 4:1, 5:1 or any other ratio greater than 1:1. The elliptical apertures 271 of the web 280 shown in FIG. 22 provide the benefit of retaining more open area than apertures having an aspect ratio of about 1:1 or less when the web 280 is extended in a direction generally orthogonal to the major axis A of the apertures 271. When strained, the major axis A shortens to a length of 2L and the minor axis lengthens to a length of 2W. However, due to the specific geometry of the apertures 271 and the stretch characteristics of the web 280, the reduction in percentage open area caused by the extension of the web 280 is significantly less than the reduction of open area of the web 180 of FIG. 20. Table I shows the effect geometry has on the open area measurements of strained and unstrained webs.

TABLE I

| Strain | Approximate Percentage Open Area |
| --- | --- |
| Circle | |
| Unstrained | 12 |
| 100% | 4 |
| Ellipse | |
| Unstrained | 24 |
| 100% | 16 |

Another factor which may affect the percentage open area, and thus, breathability of the web 80 of the present invention is the pattern of the primary apertures 71. Specifically, the pattern can influence the resultant open area as a function of a percentage strain. Thus, a certain pattern of apertures such as the staggered pattern of apertures 271 shown in FIG. 22 may provide the web 280 with a greater percentage open area when stretched than a less loosely packed or otherwise differently oriented pattern of apertures such as the pattern shown in FIG. 20.

The interconnecting elements are inherently continuous, with contiguous interconnecting elements blending into one another in mutually-adjoining transition zones or portions, e.g., transition portions 87, shown in FIG. 5. In general, transition portions are defined by the largest circle that can be inscribed tangent to any three adjacent apertures. It is understood that for certain patterns of apertures the inscribed circle of the transition portions may be tangent to more than three adjacent apertures. For illustrative purposes, interconnecting members may be thought of as beginning or ending substantially at the centers of the transition portions, such as interconnecting members 97 and 98. Likewise, the sidewalls of the interconnecting members can be described as interconnecting to sidewalls of contiguous interconnecting members at areas corresponding to points of tangency where the inscribed circle of the transition portion is tangent to an adjoining aperture.

Exclusive of the transition zones, cross-sections transverse to a center line between the beginning and end of interconnecting members are preferably of generally uniform U-shape. However, the transverse cross-section need not be uniform along the entire length of the interconnecting member, and for certain aperture configurations it will not be uniform along most of its length. For example, as can be understood from the sectional illustrations of FIG. 5, for interconnecting member 96, the width dimension, 86, of the base portion 81 may vary substantially along the length of the interconnecting member. In particular, in transition zones or portions 87, interconnecting members blend into contiguous interconnecting members and transverse cross-sections in the transition zones or portions may exhibit substantially non-uniform U-shapes, or no discernible U-shape.

Figure 8A:
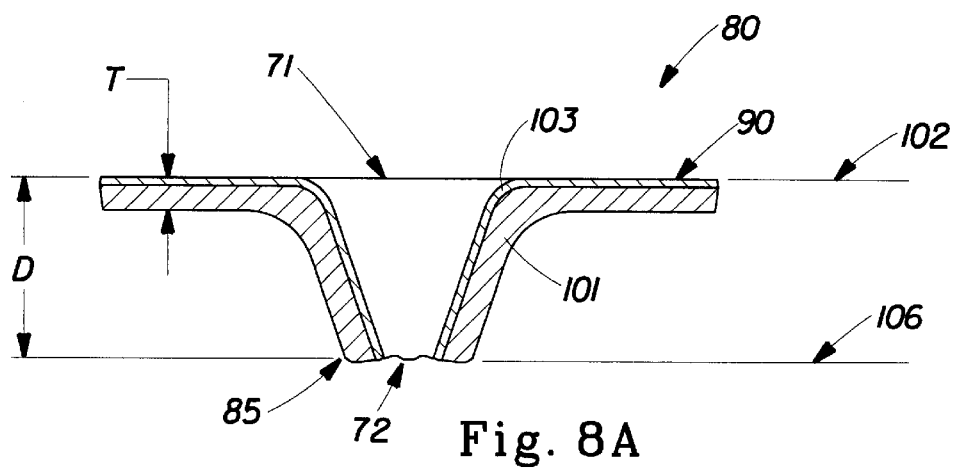
FIGS. 8A–8C are schematic representations of a cross-section of an aperture of an elastomeric web of the present invention in various states of tension.
Figure 8B:
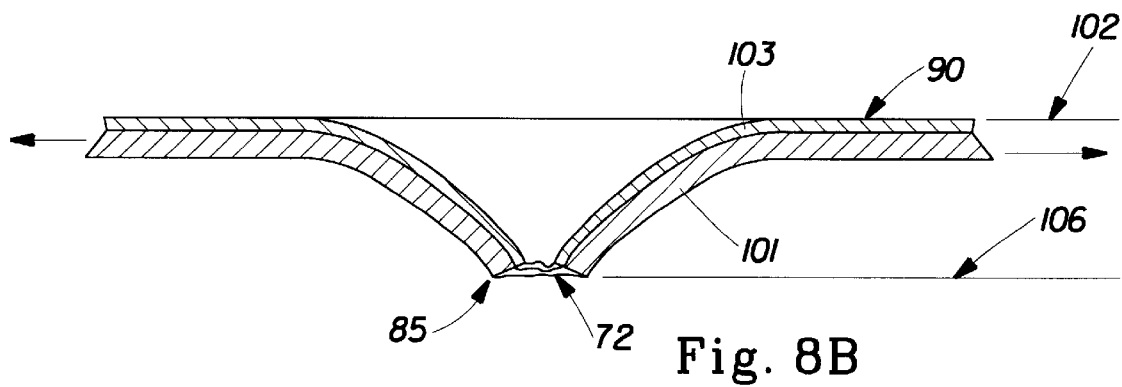
Figure 8C:
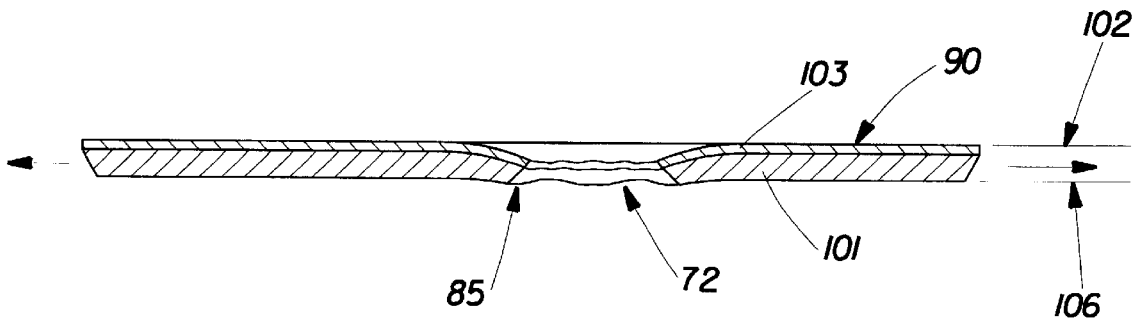

Without wishing to be bound by theory, it is believed that the web of the present invention is more reliable (i.e., resistant to catastrophic failure) when subjected to strain-induced stress due to the mechanism depicted schematically in cross section in FIGS. 8A–8C and pictorially in photomicrographs 9–11. FIG. 8A shows a primary aperture 71 in plane 102 of first surface 90, and a secondary aperture 72 in plane 106 of second surface 85, remote from plane 106 of first surface 90, of web 80 in an unstressed condition. When web 80 is stretched in the direction generally shown by arrows in FIG. 8B, first surface 90 is strained, and primary aperture 71 is likewise strained into a deformed configuration. However, the perimeter of primary aperture 71 is formed by the interconnecting members in a continuous first surface. Therefore, aperture 71 has no "edges" for tear initiation sites to compromise the elastic reliability of the web. The edges of the secondary aperture 72, being possible tear initiation sites, do not experience appreciable strain-induced stresses until the web is strained to the point where plane 102 is no longer remote from plane 106 of the first surface 90, as depicted in FIG. 8C. At the point where planes 102 and 106 are no longer remote, web 80 begins to behave essentially as a planar, apertured web.

It is instructive to consider the ratio of overall web depth, "D" in FIG. 8A, to film thickness, "T" in FIG. 8A of an unstretched elastomeric web. This ratio of D/T may be termed the draw ratio, as it pertains to the amount of film drawn out of the plane of the first surface due to the forming process of the present invention. Applicant believes that, in general, an increase in the draw ratio serves to increase resistance to tear by placing the second surface more remote from the first surface.

Without wishing to be bound by theory, it is believed that when the web 80 is strained or stretched, the elastomeric layer 101 of the present invention allows the base 81 of the interconnecting members forming a continuous web in the continuous first surface 90 to stretch. Skin layer 103 helps maintain the three-dimensional nature of the web, despite the applied stress, allowing the strain on the continuous first surface 90 and the resulting deformation of primary apertures 71 to be at least partially dissociated from the discontinuous second surface thereby minimizing strain at secondary apertures 72. Therefore the strain-induced stress at the continuous first surface of the web is substantially decoupled from potential strain-induced stress at tear initiation sites on the discontinuous second surface, at least until the secondary apertures begin to enter the plane of the first surface. This substantial dissociation, or decoupling, of the strain-induced stress of the web from strain-induced stress at the secondary apertures significantly increases web reliability by allowing repeated and sustained strains of the web up to about 400% or more without failure of the web due to tear initiation at the apertures.

Figure 9:
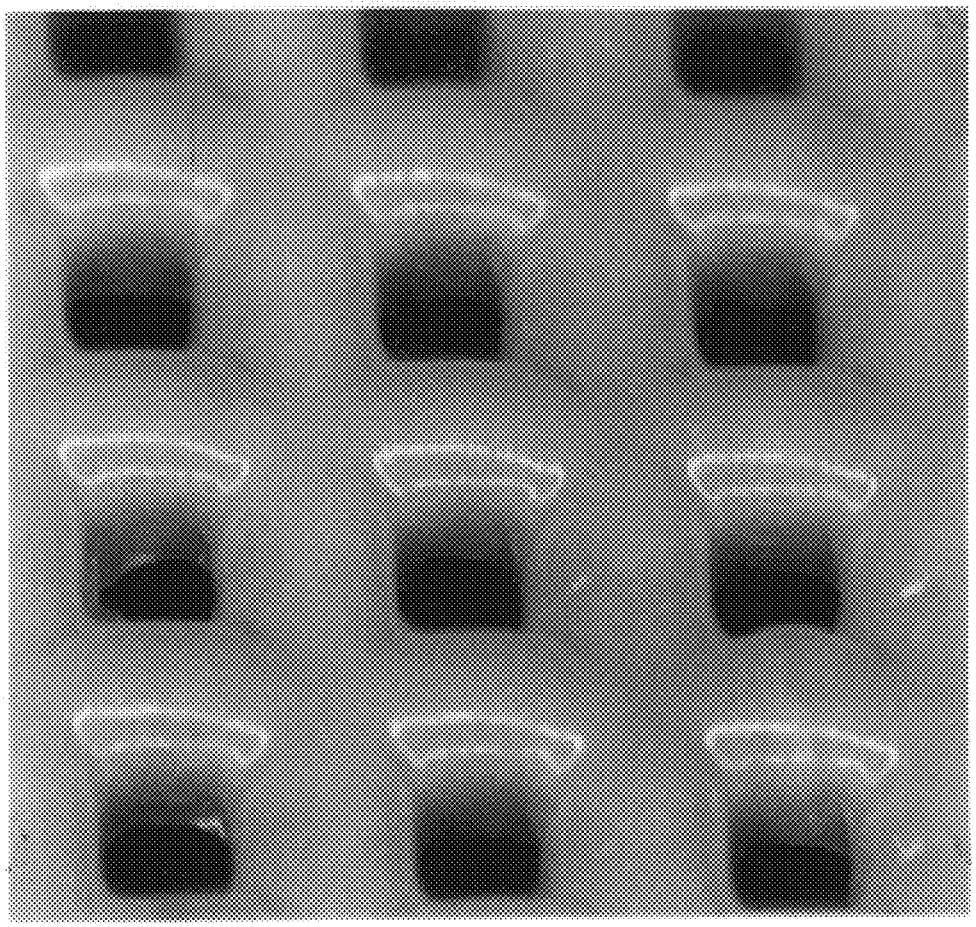
FIG. 9 is an enlarged optical photomicrograph showing the first surface of an elastomeric web of the present invention having an ordered pattern of approximately 1 mm square apertures.
Figure 10:
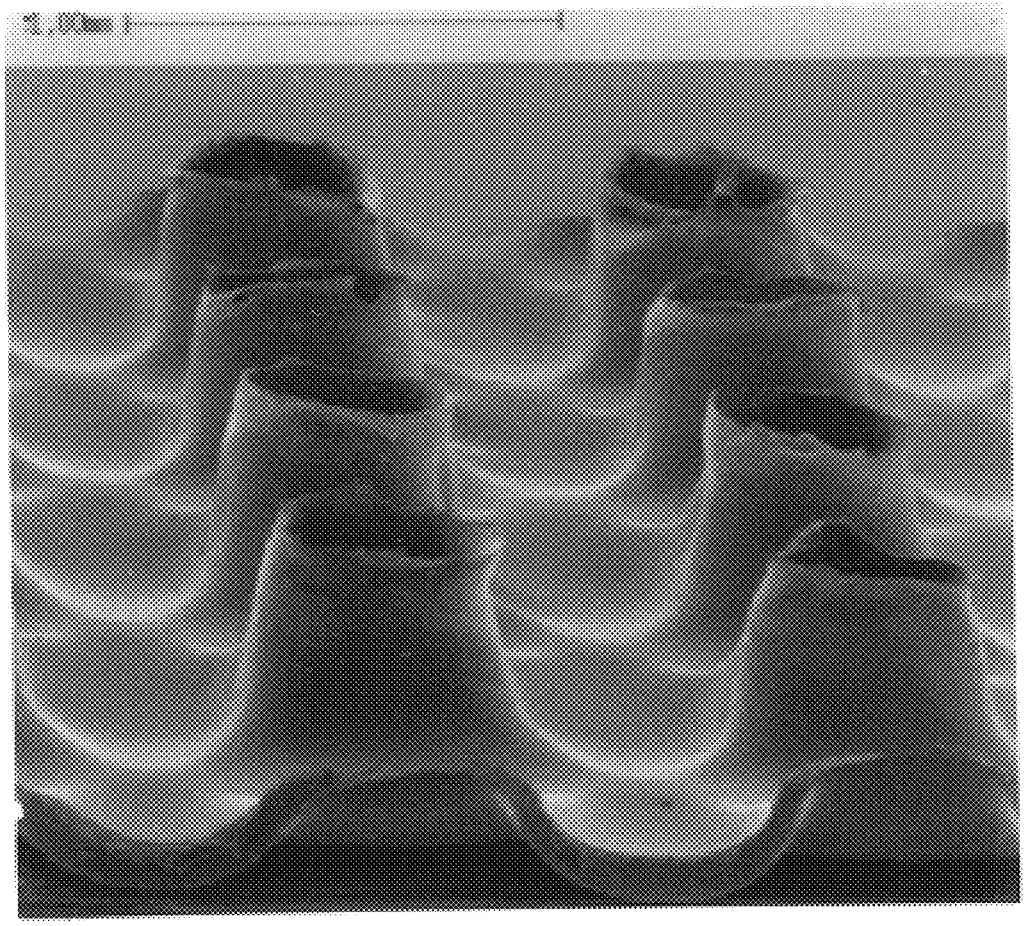
FIG. 10 is an enlarged scanning electron microscope photomicrograph perspective illustration of the second surface of the elastomeric web shown in FIG. 9 in an unstretched state.
Figure 11:
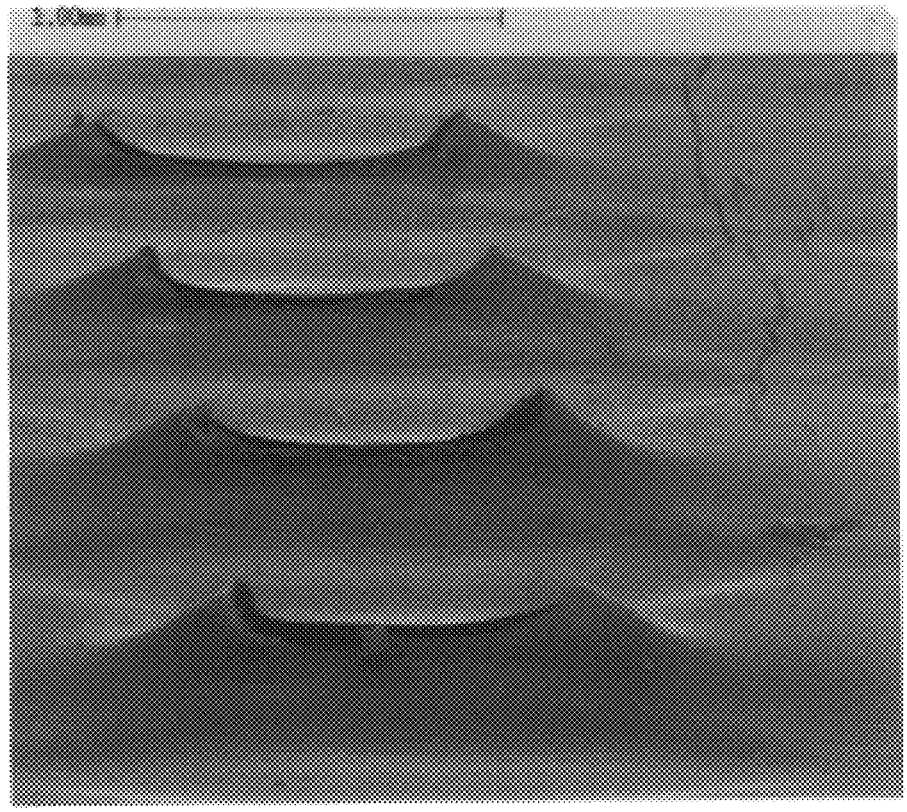
FIG. 11 is an enlarged scanning electron microscope photomicrograph perspective illustration of the second surface of the elastomeric web shown in FIG. 9 tensioned to approximately 100% strain.

The photomicrographs of FIGS. 9–11 are believed to depict visually the mechanism described schematically in FIGS. 8A–8C. FIG. 9 is an optical photomicrograph showing the first surface and primary apertures of an embodiment of the present invention. In an as-formed, unextended configuration the continuous first surface of the web embodiment shown in FIG. 9 generally forms a regular pattern of 1 mm square primary apertures spaced about 1 mm apart on all sides. FIGS. 10 and 11 are scanning electron microscope photomicrographs showing the discontinuous second surface of the web embodiment of FIG. 9, shown at a slightly different scale. FIG. 10 shows the second surface of an elastomeric web generally in a plane remote from the plane of the first surface in an unstretched state. FIG. 11 shows the second surface of a web in a state of approximately 100% strain. As shown in FIG. 11, the edges of the secondary apertures remain remote from the plane of the first surface. Although some distortion of the secondary apertures takes place, the edges remain in a substantially unstressed condition. Again, it is this substantial decoupling of the strain-induced stress of the web from strain-induced stress at the secondary apertures that significantly increases web reliability.

The differential elastic behavior of planar multilayer films or fibers having a relatively less elastic skin layer stretched beyond its elastic limit is known in the art, as described in the aforementioned U.S. Patent to Krueger et al., as well as in U.S. Pat. No. 5,376,430 to Swenson et al., issued Dec. 27, 1994 and U.S. Pat. No. 5,352,518 to Muramoto et al., issued Oct. 4, 1994. As shown in the art, upon recovery after extension beyond the elastic limits of the skin layer, the skin layer may form a microscopic microtexture of peak and valley irregularities, due to the resulting increased surface area of the skin layer relative to the elastomeric layer.

Figure 12:
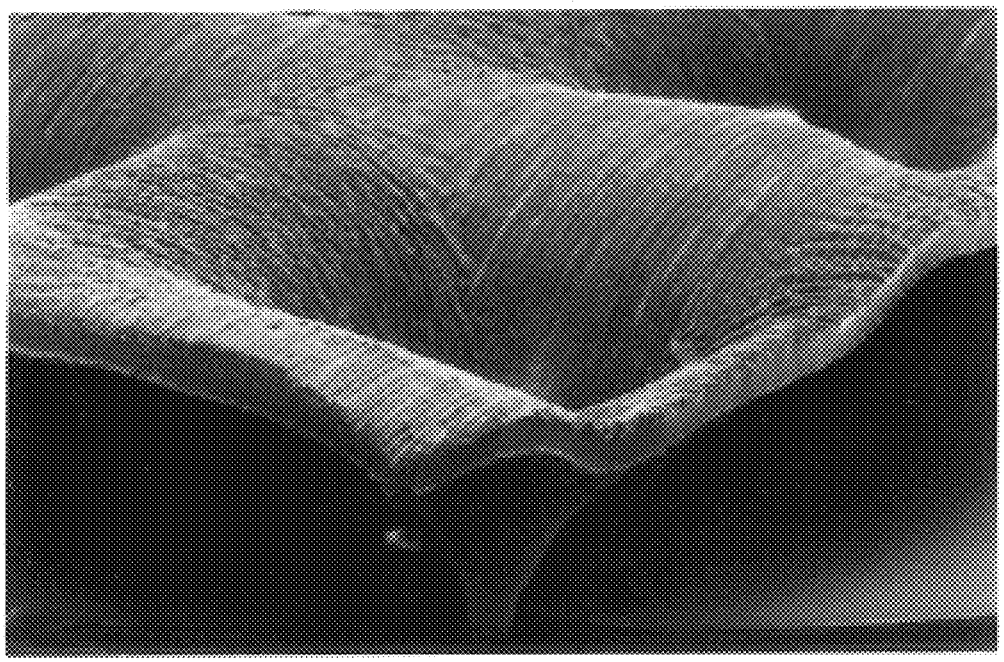
FIG. 12 is an enlarged scanning electron microscope photomicrograph perspective illustration of an aperture of an elastomeric web of the present invention showing rugosities formed after extension and recovery.

Likewise, when a web of the present invention is strained for the first time, the skin layer of the strained portion may be stressed beyond its elastic limit. The elastomeric layer allows the web to return substantially to its pre-stressed, macroscopic, three-dimensional configuration, but the portions of the skin layer that were stressed beyond their elastic limit may not return to a pre-stressed configuration due to the excess material created in the inelastic strain. Upon recovery after extension, the skin layer forms microscopic microtexture of peak and valley irregularities, more generally described as transversely-extending rugosities, as shown in the photomicrograph of FIG. 12. The rugosities form on the interconnecting members in substantially uniform patterns generally transverse to the direction of stretch, and generally radially disposed about the primary apertures. Depending on the degree of strain on the web, the rugosities may be limited to substantially the continuous first surface of the web, or more generally may extend over substantially the entire surface of the interconnecting members.

Without being bound by theory, it is believed that the transversely-extending rugosities are beneficial to the elastomeric web for at least two reasons. First, the rugosities impart a softer overall texture or feel to the elastomeric web. Second, the rugosities, being radially disposed to the primary apertures, and extending toward the secondary apertures, may facilitate better fluid handling characteristics when used as a body-contacting web of a disposable absorbent article.

Figure 13:
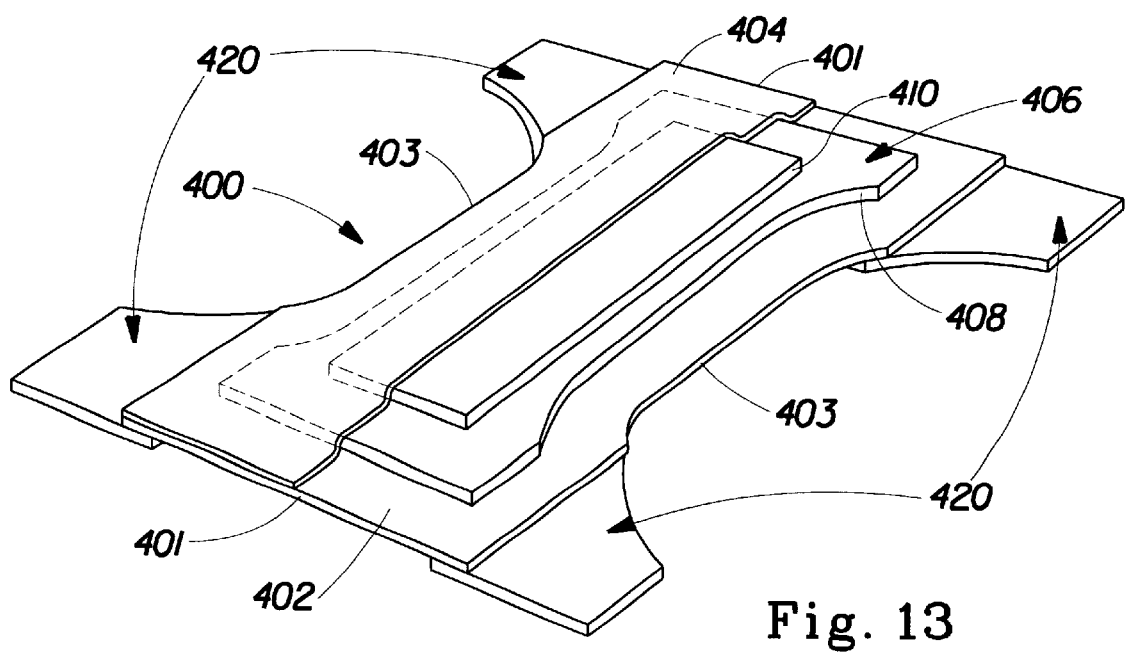
FIG. 13 is a partially segmented perspective illustration of a disposable garment comprising the elastomeric web of the present invention.

A representative embodiment of an elastomeric web of the present invention utilized in a disposable absorbent article in the form of a diaper 400, is shown in FIG. 13. As used herein, the term "diaper" refers to a garment generally worn by infants and incontinent persons that is worn about the lower torso of the wearer. It should be understood, however, that the elastomeric web of the present invention is also applicable to other absorbent articles such as incontinent briefs, training pants, sanitary napkins, and the like. The diaper 400 depicted in FIG. 13 is a simplified absorbent article that could represent a diaper prior to its being placed on a wearer. It should be understood, however, that the present invention is not limited to the particular type or configuration of diaper shown in FIG. 13. A particularly preferred representative embodiment of a disposable absorbent article in the form of a diaper is taught in U.S. Pat. No. 5,151,092, to Buell et al., issued Sep. 29, 1992, being hereby incorporated herein by reference.

FIG. 13 is a perspective view of the diaper 400 in its uncontracted state (i.e., with all the elastic induced contraction removed) with portions of the structure being cut-away to more clearly show the construction of the diaper 400. The portion of the diaper 400 which contacts the wearer faces the viewer. The diaper 400 is shown in FIG. 13 to preferably comprise a liquid pervious topsheet 404; a liquid impervious backsheet 402 joined with the topsheet 404; and an absorbent core 406 positioned between the topsheet 404 and the backsheet 402. Additional structural features such as elastic leg cuff members 405, waist feature 409 and and fastening means for securing the diaper in place upon a wearer may also be included.

While the topsheet 404, the backsheet 402, and the absorbent core 406 can be assembled in a variety of well known configurations, a preferred diaper configuration is described generally in U.S. Pat. No. 3,860,003 to Buell, issued Jan. 14, 1975, the disclosure of which is incorporated by reference. Alternatively preferred configurations for disposable diapers herein are also disclosed in U.S. Pat. No. 4,808,178 to Aziz et al., issued Feb. 28, 1989; U.S. Pat. No. 4,695,278 to Lawson, issued Sep. 22, 1987; and U.S. Pat. No. 4,816,025 to Foreman, issued Mar. 28, 1989, the disclosures of each of these patents hereby being incorporated herein by reference.

FIG. 13 shows a representative embodiment of the diaper 400 in which the topsheet 404 and the backsheet 402 are co-extensive and have length and width dimensions generally larger than those of the absorbent core 406. The topsheet 404 is joined with and superimposed on the backsheet 402 thereby forming the periphery of the diaper 400. The periphery defines the outer perimeter or the edges of the diaper 400. The periphery comprises the end edges 401 and the longitudinal edges 403.

The size of the backsheet 402 is dictated by the size of the absorbent core 406 and the exact diaper design selected. In a preferred embodiment, the backsheet 402 has a modified hourglass-shape extending beyond the absorbent core 406 a minimum distance of at least about 1.3 centimeters to about 2.5 centimeters (about 0.5 to about 1.0 inch) around the entire diaper periphery.

The topsheet 404 and the backsheet 402 are joined together in any suitable manner. As used herein, the term "joined" encompasses configurations whereby the topsheet 404 is directly joined to the backsheet 402 by affixing the topsheet 404 directly to the backsheet 402, and configurations whereby the topsheet 404 is indirectly joined to the backsheet 402 by affixing the topsheet 404 to intermediate members which in turn are affixed to the backsheet 402. In a preferred embodiment, the topsheet 404 and the backsheet 402 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 404 to the backsheet 402.

End edges 401 form a waist region, which in a preferred embodiment comprise a pair of elastomeric side panels 420, which extend laterally from end edges 401 of diaper 400 in an extended configuration. In a preferred embodiment elastomeric side panels 420 comprise the elastomeric web of the present invention. In an especially preferred embodiment, when used as elastomeric side panels, the web 80 of the present invention is further processed to form a composite laminate by bonding it on one, or preferably both sides thereof, with fibrous nonwoven materials to form a soft, compliant elasticized member, utilizing methods known in the art, such as adhesive bonding.

Fibrous nonwoven materials suitable for use in a composite laminate of the present invention include nonwoven webs formed of synthetic fibers (such as polypropylene, polyester, or polyethylene), natural fibers (such as wood, cotton, or rayon), or combinations of natural and synthetic fibers. Suitable nonwoven materials can be formed by various processes such as carding, spun-bonding, hydroentangling, and other processes familiar to those knowledgeable in the art of nonwovens. A presently preferred fibrous nonwoven material is carded polypropylene, commercially available from Fiberweb of Simpsonville, S.C.

Fibrous nonwoven materials may be bonded to the elastomeric web by any one of various bonding methods known in the art. Suitable bonding methods include adhesive bonding such as by a uniform continuous layer of adhesive, a patterned layer of adhesive, or an array of separate lines, spirals, or spots of adhesive, or other methods such as heat bonds, pressure bonds, ultrasonic bonds, dynamic mechanical bonds, or any other suitable attachment means or combinations of these attachment means as are known in the art. Representative bonding methods are also described in PCT application WO 93/09741, entitled "Absorbent Article Having a Nonwoven and Apertured Film Coversheet", published May 27, 1993 naming Aziz et al. as inventors, and being hereby incorporated herein by reference.

After bonding to a fibrous nonwoven material, the composite web may tend to be less elastomeric due to the relative inelasticity of the bonded nonwoven. To render the nonwoven more elastic, and to restore elasticity to the composite laminate, the composite web may be processed by methods and apparatus used for elasticizing "zero strain" laminates by incremental stretching, as disclosed in the aforementioned Buell et al. '092 patent, as well as the aforementioned Weber et al. '897, Buell et al. '793, and Weber et al. '679 patents. The resulting elasticized "zero-strain" composite web then has a soft, cloth-like feel for extended use and comfortable fit in an absorbent garment.

Figure 14:
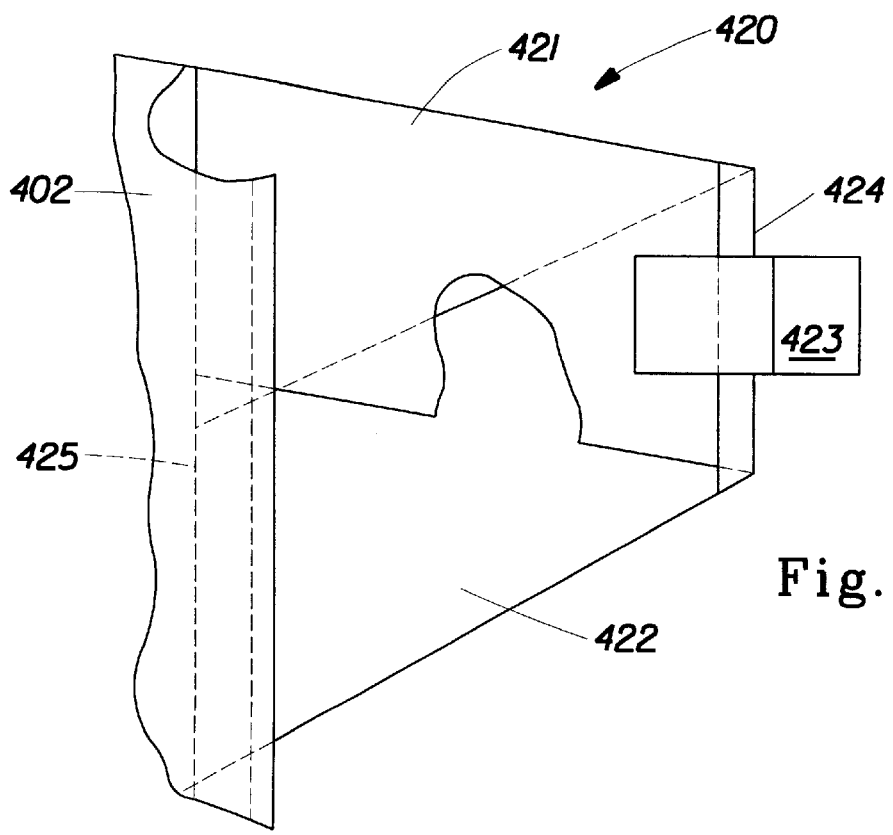
FIG. 14 is a simplified, partially segmented illustration of a preferred embodiment of side panels for a disposable garment.

Side panels 420 may be joined to the diaper in any suitable manner known in the art. For example, as shown in FIG. 13, side panels 420 may be affixed directly to the backsheet 402 by attachment means such as an adhesive or any other attachment means as known in the art. A particularly preferred configuration for side panels 420 is shown in FIG. 14, a configuration which is more fully disclosed in commonly assigned, co-pending U.S. Pat. No. 5,669,897 issued to LaVon et al. on Sep. 23, 1997, and Ser. No. 08/155,048, filed Nov. 19, 1993, the disclosures of both being hereby incorporated herein by reference.

As shown in FIG. 14, side panel 420 may be comprised of two webs or strips, 421 and 422. Strips 421 and 422 may be two discrete strips, or alternatively they may be formed by bending a single strip at leading edge 424, and offsetting the two resulting strip lengths in a non-parallel manner. If two discrete strips are used, they may be bonded, as with suitable adhesive, to one another at leading edge 424, and may simultaneously be bonded to tape tab 423. Side panel 420 may be bonded to backsheet 402 at bond area 425 in any suitable manner, and particularly as disclosed in the aforementioned LaVon et al. '346 patent application. While it is not necessary that the pairs of side panels be identical, they are preferably mirror images one of the other.

Tape fasteners, e.g., tape tab 423, are typically applied to at least one pair of elastomeric side panels 420 to provide a fastening means for holding the diaper on the wearer. The tape tab fasteners can be any of those well known in the art, such as the fastening tape disclosed in the aforementioned Buell '092 patent, and U.S. Pat. No. 3,848,594 to Buell, issued Nov. 19, 1974, the disclosure of which is hereby incorporated by reference.

Other elastic members, of the present invention may be disposed adjacent the periphery of the diaper 400. Elastic members are preferably along each longitudinal edge 403, so that the elastic members tend to draw and hold the diaper 400 against the legs of the wearer. In addition, the elastic members can be disposed adjacent either or both of the end edges 401 of the diaper 400 to provide a waistband 409 as well as or rather than leg cuffs. For example, a suitable waistband is disclosed in U.S. Pat. No. 4,515,595 to Kievit et al., issued May 7, 1985, the disclosure of which is hereby incorporated by reference. In addition, a method and apparatus suitable for manufacturing a disposable diaper having elastically contractible elastic members is described in U.S. Pat. No. 4,081,301 to Buell, issued Mar. 28, 1978, the disclosure of which is hereby incorporated herein by reference.

The elastic members are secured to the diaper 400 in an elastically contractible condition so that in a normally unrestrained configuration, the elastic members effectively contract or gather the diaper 400. The elastic members can be secured in an elastically contractible condition in at least two ways. For example, the elastic members can be stretched and secured while the diaper 400 is in an uncontracted condition. In addition, the diaper 400 can be contracted, for example, by pleating, and the elastic members secured and connected to the diaper 400 while the elastic members are in their relaxed or unstretched condition. The elastic members may extend along a portion of the length of the diaper 400. Alternatively, the elastic members can extend the entire length of the diaper 400, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or non-parallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 400 using a variety of bonding patterns or the elastic members can simply be glued to the diaper 400.

As shown in FIG. 13, the absorbent core 406 preferably includes a fluid distribution member 408. In a preferred configuration such as depicted in FIG. 13, the absorbent core

406 preferably further includes an acquisition layer or member 410 in fluid communication with the fluid distribution member 408 and located between the fluid distribution member 408 and the topsheet 404. The acquisition layer or member 410 may be comprised of several different materials including nonwoven or woven webs of synthetic fibers including polyester, polypropylene, or polyethylene, natural fibers including cotton or cellulose, blends of such fibers, or any equivalent materials or combinations of such materials.

In use, the diaper 400 is applied to a wearer by positioning the back waistband region under the wearer's back, and drawing the reminder of the diaper 400 between the wearer's legs so that the front waistband region is positioned across the front of the wearer. The elastomeric side panels are then extended as necessary for comfort and fit, and the tape-tab or other fasteners are then secured preferably to outwardly facing areas of the diaper 400. By having side panels 420, leg cuffs 405 or one or more waistbands 409 comprising an elastomeric web of the present invention, the diaper may be adapted for differing sizes of children, for example, in a manner providing for close, comfortable fit with breathability.

As described above, the breathability of the web 80, and thus the portion of the diaper 20 including the web 80 can be increased by providing the web with apertures 71 which are of a certain geometry and orientation. In order to provide the greatest breathability in the elasticized side panels 420, waistband 409 or any other elasticized feature, the web 80 should include primary apertures 71 having a major axis A and a minor axis B which are different from each other. Preferably, the aspect ratio of the major axis A to the minor axis B should be greater than 1:1, preferably greater than about 1.5:1 and may be about 2:1, 3:1, 4:1, 5:1 or greater. The major axis A of the primary apertures 71 should be oriented generally orthogonal to the direction which the web is extended during use. For example, in FIG. 24, the waistband 409 includes web 80. Web 80 includes a plurality of primary apertures 71 in a stacked pattern 412. The apertures 71 are oriented such that the major axis A is generally orthogonal to the direction E of the extension of the waistband 409. It may also be desirable to provide the web 80 with apertures in a particular pattern. Preferred patterns for increasing the breathability of the web include stacked and staggered patterns as shown in FIGS. 20–25.

Figure 25:
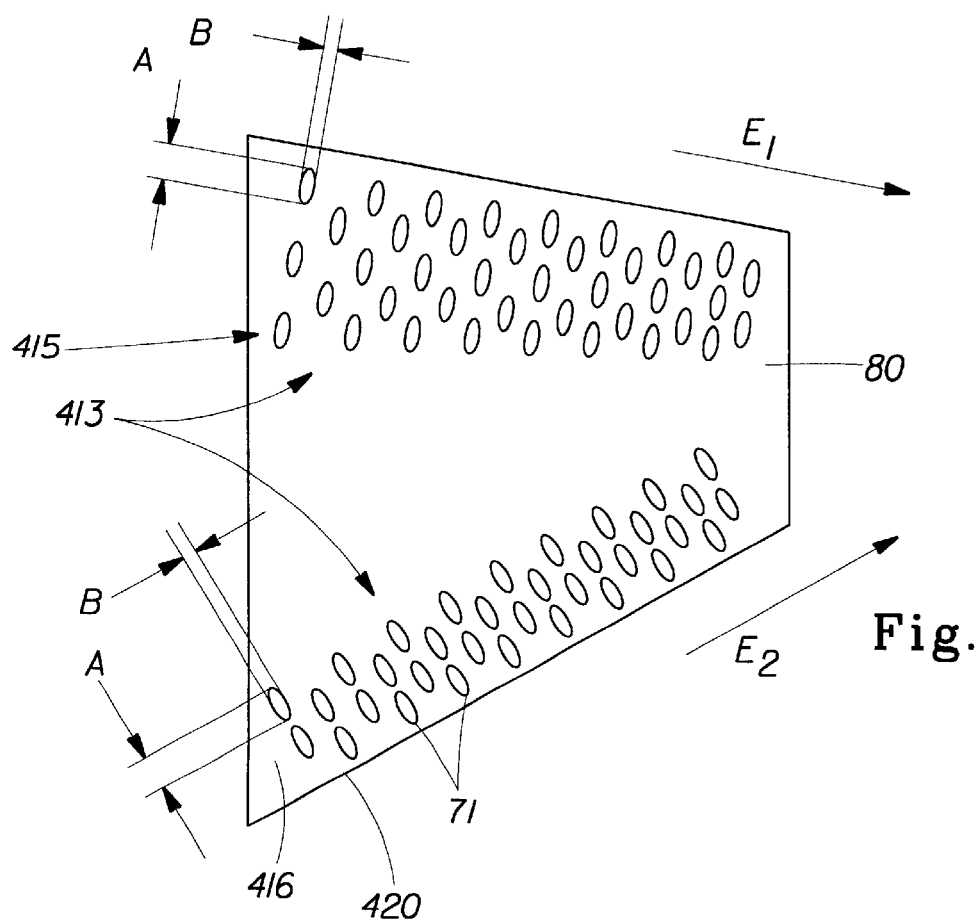
FIG. 25 is a simplified, partially segmented illustration of a side panel of a disposable article.

In another example, shown in FIG. 25, the web 80 is disposed in the side panel 420. The side panel 420 has two different directions of extension, $E_1$ and $E_2$.

Direction $E_1$ is the direction of extension corresponding to movements of the hip of the wearer, whereas direction $E_2$ corresponds to the extension provided by the wearer's thigh. (It should be noted that the side panel 420 may include one or any number of directions of extension.) Thus, the side panel 420 is provided with web 80 having patterns 413 of apertures 71 oriented differently. In the hip region 415, the apertures 71 are oriented such that the major axis A of the apertures 71 is generally orthogonal to the direction of extension $E_1$. In the thigh area 416, the major axis A of the apertures 71 is oriented such that it is generally orthogonal to the direction of extension $E_2$. The same benefit of greater breathability can be achieved in waistbands, leg cuffs and other extensible features of disposable articles.

While a disposable diaper is shown as a preferred embodiment of a garment comprising an elastomeric web of the present invention, this disclosure is not meant to be limiting to disposable diapers. Other disposable garments such as pull on diapers, training pants, sanitary napkins, bandages and the like may also incorporate an elastomeric web of the invention in various parts to give added comfort, fit and breathability. As well, it is contemplated that even durable garments such as undergarments and swimwear may benefit from the durable porous, extensible characteristics of an elastomeric web of the present invention.

The multilayer film 120 of the present invention may be processed using conventional procedures for producing multilayer films on conventional coextruded film-making equipment. In general, polymers can be melt processed into films using either cast or blown film extrusion methods both of which are described in "Plastics Extrusion Technology"— 2nd Ed., by Allan A. Griff (Van Nostrand Reinhold—1976), which is hereby incorporated herein by reference. Cast film is extruded through a linear slot die. Generally, the flat web is cooled on a large moving polished metal roll. It quickly cools, and peels off the first roll, passes over one or more auxiliary rolls, then through a set of rubber-coated pull or "haul-off" rolls, and finally to a winder.

In blown film extrusion the melt is extruded upward through a thin annular die opening. This process is also referred to as tubular film extrusion. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattened frame through a pair of pull rolls and into a winder.

A coextrusion process requires more than one extruder and either a coextrusion feedblock or a multi-manifold die system or combination of the two to achieve the multilayer film structure. U.S. Pat. Nos. 4,152,387 and 4,197,069, issued May 1, 1979 and Apr. 8, 1980, respectively, both to Cloeren, are hereby incorporated herein by reference, disclose the feedblock principle of coextrusion. Multiple extruders are connected to the feedblock which employs moveable flow dividers to proportionally change the geometry of each individual flow channel in direct relation to the volume of polymer passing through said flow channels. The flow channels are designed such that at their point of confluence, the materials flow together at the same flow rate and pressure eliminating interfacial stress and flow instabilities. Once the materials are joined in the feedblock, they flow into a single manifold die as a composite structure. It is important in such processes that the melt viscosities and melt temperatures of the material do not differ too greatly. Otherwise flow instabilities can result in the die leading to poor control of layer thickness distribution in the multilayer film.

An alternative to feedblock coextrusion is a multi-manifold or vane die as disclosed in aforementioned U.S. Pat. Nos. 4,152,387, 4,197,069, as well as U.S. Pat. No. 4,533,308, issued Aug. 6, 1985 to Cloeren, hereby incorporated herein by reference. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same linear flow rate, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer can be completely surrounded by the outer layer leaving no exposed edges. The aforementioned patents also disclose the combined use of feedblock systems and vane dies to achieve more complex multilayer structures.

The multilayer films of the present invention may comprise two or more layers, at least one of the layers being elastomeric. Although an elastomeric layer is generally substantially joined to one or two skin layers, it is contemplated that multiple elastomeric layers may be utilized, each elastomeric layer being joined to one or two skin layers. Three-layer films, like multilayer film 120 shown in FIG. 4, preferably comprise a central elastomeric core 101 that may comprise from about 10 to 90 percent of the total thickness of the film. Outer skin layers 103 are generally, but not necessarily, identical and may comprise from about 5 to 45 percent of the total thickness of the film. Tie layers, when employed, may each comprise from bout 5 to 10 percent of the total film thickness. In a three-layer film, core layer 101 has opposed first and second sides, one side being substantially continuously joined to one side of each outer skin layer 103 prior to the application of applied stress to the web.

After the multilayer elastomeric film has been coextruded it is preferably fed to a forming structure for aperturing and cooling, thereby producing a macroscopically-expanded, three-dimensional, apertured elastomeric web of the present invention. In general the film may be formed by drawing such film against a forming screen or other forming structure by means of a vacuum and passing an air or water stream over the outwardly posited surface of the film. Such processes are described in the aforementioned Radel et al. patent as well as in U.S. Pat. No. 4,154,240, issued to Lucas et al., both hereby incorporated herein by reference. Forming a three-dimensional elastomeric web may alternatively be accomplished by applying a liquid stream with sufficient force and mass flux to cause the web formation as disclosed in commonly assigned U.S. Pat. No. 4,695,422, issued to Curro et al. and hereby incorporated herein by reference. Alternatively, the film can be formed as described in commonly assigned U.S. Pat. No. 4,552,709 to Koger et al., and hereby incorporated herein by reference. Preferably the elastomeric web is uniformly macroscopically expanded and apertured by the method of supporting the forming structure in a fluid pressure differential zone by a stationary support member as taught by commonly assigned U.S. Pat. Nos. 4,878,825 and 4,741,877, both to Mullane, Jr., and hereby incorporated herein by reference.

Although not shown, the process of the present invention, using a conventional forming screen having a woven wire support structure, would also form a web within the scope of the present invention. The knuckles of a woven wire forming screen would produce a macroscopically-expanded, three-dimensional web having a pattern of undulations in the first surface, the undulations corresponding to the knuckles of the screen. However, the undulations would remain generally in the plane of the first surface, remote from the plane of the second surface. The cross-section of the interconnecting members would remain generally upwardly concave-shaped with the interconnecting sidewalls of the interconnecting members terminating to form secondary apertures substantially in the plane of the second surface.

Figure 15:
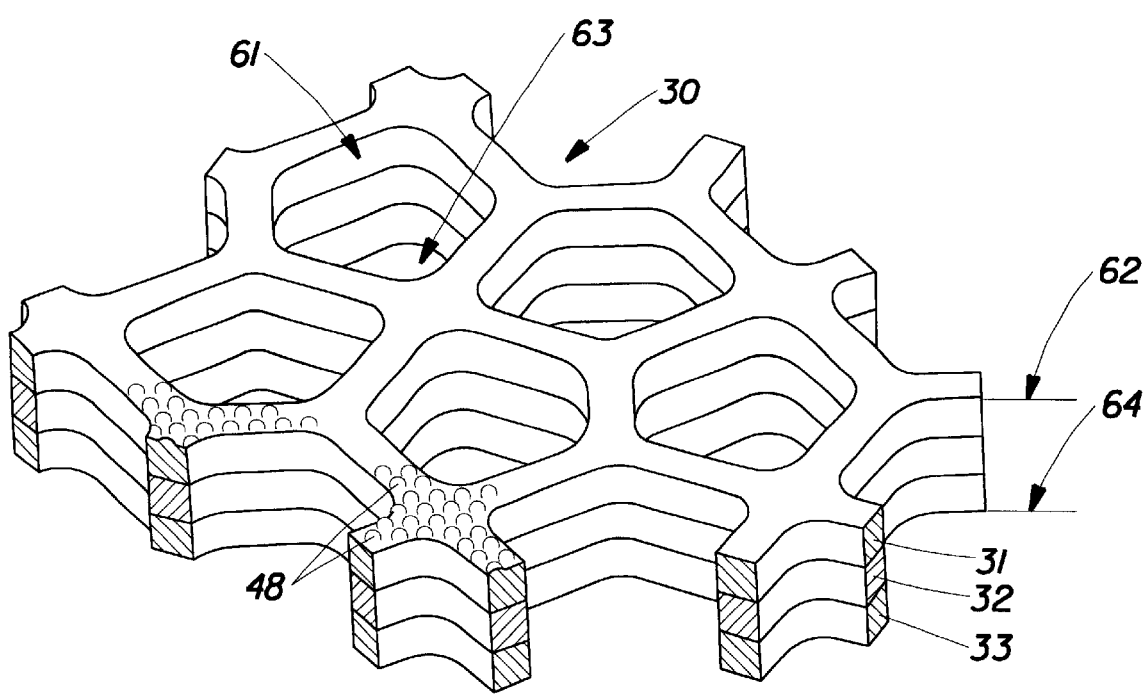
FIG. 15 is a simplified, partially exploded perspective illustration of a laminate structure generally useful for forming the web structure illustrated in FIG. 2.

A particularly preferred forming structure comprises a photoetched laminate structure as shown in FIG. 15, showing an enlarged, partially segmented, perspective illustration of a photoetched laminate structure of the type used to form plastic webs of the type generally illustrated in FIG. 2. The laminate structure 30 is preferably constructed generally in accordance with the teachings of the aforementioned Radel et al. patent, and is comprised of individual lamina 31, 32, and 33. A comparison of FIG. 3 with the elastomeric web 80 shown in FIG. 2 reveals the correspondence of primary aperture 71 in plane 102 of the elastomeric web 80 to opening 61 in the uppermost plane 62 of the photoetched laminate structure 30. Likewise, aperture opening 72 in plane 106 of elastomeric web 80 corresponds to opening 63 in lowermost plane 64 of photoetched laminate structure 30.

The uppermost surface of photoetched laminate structure 30 located in uppermost plane 62 may be provided with a microscopic pattern of protuberances 48 without departing from the scope of the present invention. This is preferably accomplished by applying a resist coating which corresponds to the desired microscopic pattern of surface aberrations to the top side of a planar photoetched lamina 31, and thereafter initiating a second photoetching process. The second photoetching process produces a lamina 31 having a microscopic pattern of protuberances 48 on the uppermost surface of the interconnected elements defining the pentagonally shaped apertures, e.g., aperture 41. The microscopic pattern of protuberances does not substantially remove the first surface from the plane of the first surface. The first surface is perceived on a macroscopic scale, while the protuberances are perceived on a microscopic scale. Construction of a laminate structure employing such a pattern of protuberance 48 on its uppermost layer is generally disclosed in the aforementioned Ahr et al. patent.

Figure 16:
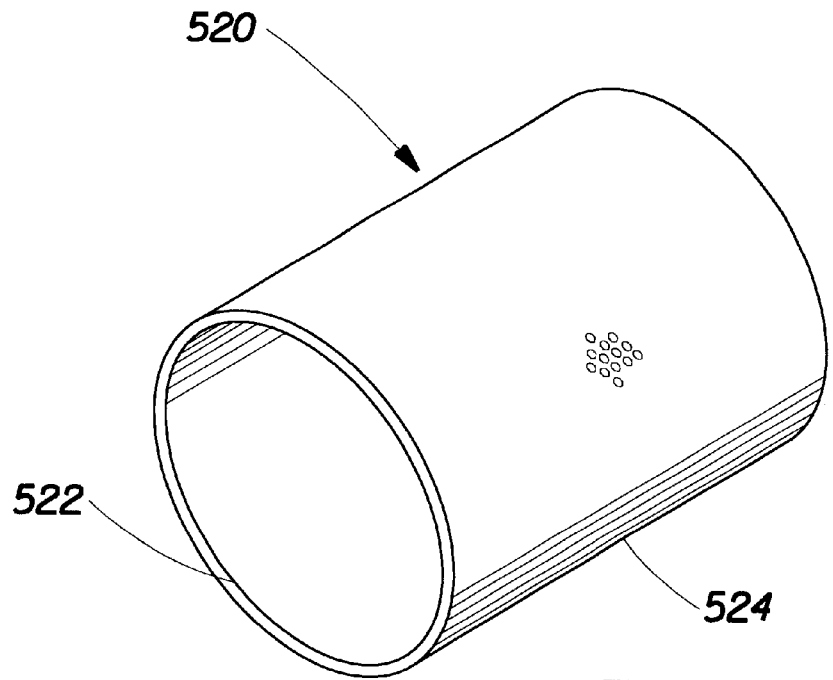
FIG. 16 is a perspective view of a tubular member formed by rolling a planar laminate structure of the type generally illustrated in FIG. 15 to the desired radius of curvature and joining the free ends thereof to one another.

Processes for constructing laminate structures of the type generally disclosed in FIG. 2 are disclosed in the aforementioned Radel et al. patent. The photoetched laminate structures are preferably rolled by conventional techniques into a tubular forming member 520, as illustrated generally in FIG. 16 and their opposing ends joined generally in accordance with the teachings of Radel et al. to produce a seamless tubular forming member 520.

Figure 17:
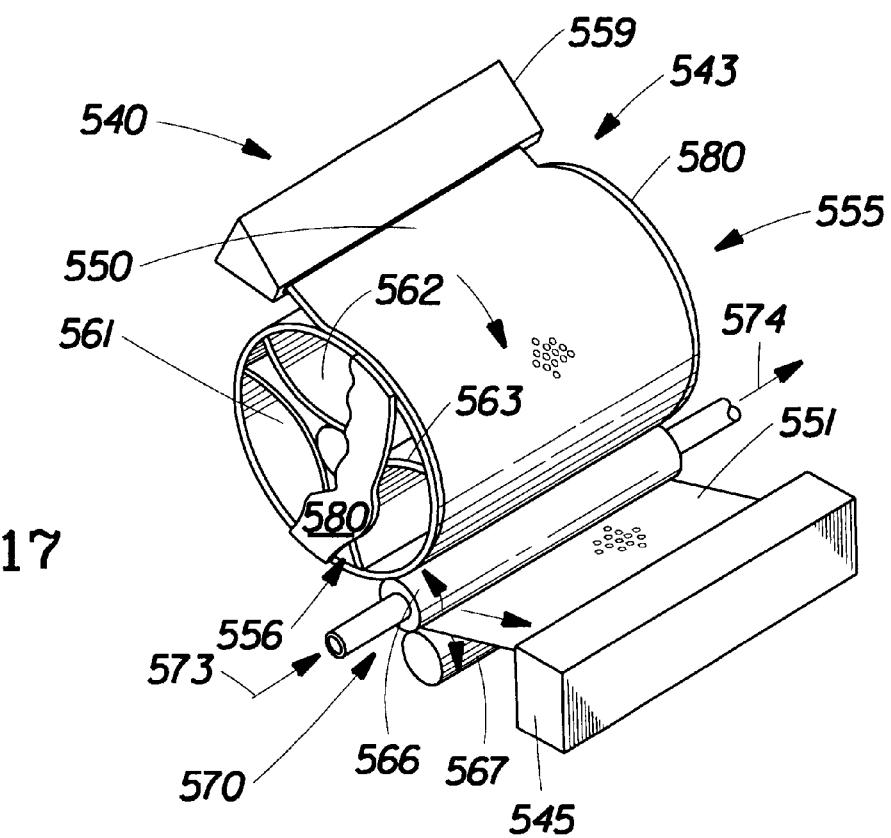
FIG. 17 is a simplified schematic illustration of a preferred method and apparatus for debossing and perforating an elastomeric film generally in accordance with the present invention.

The outermost surface 524 of the tubular forming member 520 is utilized to form the multilayer elastomeric web brought in contact therewith while the innermost surface 522 of the tubular member generally does not contact the plastic web during the forming operation. The tubular member may, in a preferred embodiment of the present invention, be employed as the forming surface on debossing/perforating cylinder 555 in a process of the type described in detail in the aforementioned Lucas et al. patent. A particularly preferred apparatus 540 of the type disclosed in said patent is schematically shown in FIG. 17. It includes debossing and perforating means 543, and constant tension film forwarding and winding means 545 which may, if desired, be substantially identical to and function substantially identically to the corresponding portions of the apparatus shown and described in U.S. Pat. No. 3,674,221 issued to Riemersma on Jul. 4, 1972 and which is hereby incorporated herein by reference. The frame, bearing, supports and the like which must necessarily be provided with respect to the functional members of apparatus 540 are not shown or described in detail in order to simplify and more clearly depict and disclose the present invention, it being understood that such details would be obvious to persons of ordinary skill in the art of designing plastic film converting machinery.

Briefly, apparatus 540, schematically shown in FIG. 17, comprises means for continuously receiving a ribbon of thermoplastic film 550 from coextruder 559, for example, and converting it into a debossed and perforated film 551. Film 550 is preferably supplied directly from the coextrusion process while still above its thermoplastic temperature so as to be vacuumed formed prior to cooling. Alternatively, film 550 may be heated by directing hot air jets against one surface of the film while applying vacuum adjacent the opposite surface of the film. To maintain sufficient control of film 550 to substantially obviate wrinkling and/or macroscopically distending the film, apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The tension is required to control and smooth a running ribbon of thermoplastic film; the zero tension zone results from the film in the zone being at a sufficiently high temperature to enable debossing and perforating the film.

As can be seen in FIG. 17, the debossing and perforating means 543 includes a rotatably mounted debossing perforating cylinder 555 having closed ends 580, a nonrotating triplex vacuum manifold assembly 556 and optional hot air jet means (not shown). The triplex vacuum manifold assembly 556 comprises three manifolds designated 561, 562, and 563. Also shown in FIG. 17 is a power rotated lead-off/chill roll 566 and a soft-face (e.g., low density neoprene) roll 567 which is driven with the chill roll. Briefly, by providing means (not shown) for independently controlling the degree of vacuum in the three vacuum manifolds, a thermoplastic ribbon of film running circumferentially about a portion of the debossing-perforating cylinder 555 is sequentially subjected to a first level of vacuum by manifold 561, a second level of vacuum by manifold 562, and a third level of vacuum by manifold 563. As will be described more fully hereinafter, the vacuum applied to the film by manifold 561 enables maintaining upstream tension in the film, vacuum applied by manifold 562 enables perforating the film, and vacuum applied by manifold 563 enables cooling the film to below its thermoplastic temperature and enables establishing downstream tension therein. If desired, the film contacting surface of the debossing-perforating cylinder 555 may be preheated prior to reaching vacuum manifold 562 by means well known in the art (and therefore not shown) to facilitate better conformance of plastic films comprised of flow-resistant polymers during the debossing operation. The nip 570 intermediate chill roll 566 and the soft-face roll 567 is only nominally loaded because high pressure would iron-out the three-dimensional debossments which are formed in the film in the aforementioned manner. However, even nominal pressure in nip 570 helps the vacuum applied by manifold 563 to isolate downstream tension (i.e., roll winding tension) from the debossing-perforating portion of the debossing-perforating cylinder 555, and enables the nip 570 to peel the debossed and perforated film from the debossing-perforating cylinder 555. Moreover, while vacuum drawn ambient air passing through the film into manifold 563 will normally cool the film to below its thermoplastic temperature, the passage of coolant through the chill roll as indicated by arrows 573, 574 in FIG. 17 will enable the apparatus to handle thicker films or be operated at higher speeds.

The debossing and perforating means 543 comprises the rotatably mounted debossing-perforating cylinder 555, means (not shown) for rotating the cylinder 555 at a controlled peripheral velocity, the non-rotating triplex vacuum manifold assembly 556 inside the debossing-perforating cylinder 555, means (not shown) for applying controlled levels of vacuum inside the three vacuum manifolds 561, 562 and 563 comprising the triplex manifold assembly 556, and optional hot air jet means (not shown). The debossing-perforating cylinder 555 may be constructed by generally following the teachings of the aforementioned Lucas et al. patent, but substituting a tubular laminate forming surface of the present invention for the perforated tubular forming surface disclosed therein.

To summarize, the first vacuum manifold 561, and the third vacuum manifold 563 located within the debossing-perforating cylinder 555 enable maintaining substantially constant upstream and downstream tension, respectively, in a running ribbon of film while the intermediate portion of the film adjacent the second vacuum manifold 562 within the debossing-perforating cylinder 555 is subjected to tension vitiating heat and vacuum to effect debossing and perforating of the film.

While a preferred application of the disclosed photoetched laminate structure is in a vacuum film forming operation as generally outlined in the aforementioned commonly assigned patent issued to Lucas et al., it is anticipated that photoetched laminate forming structures of the present invention could be employed with equal facility to directly form a three-dimensional plastic structure of the present invention. Such a procedure would involve applying a heated fluid plastic material, typically a thermoplastic resin, directly to the forming surface applying a sufficiently great pneumatic differential pressure to the heated fluid plastic material to cause said material to conform to the image of the perforate laminate forming surface, allowing the fluid material to solidify, and thereafter removing the three-dimensional plastic structure from the forming surface.

Figure 18:
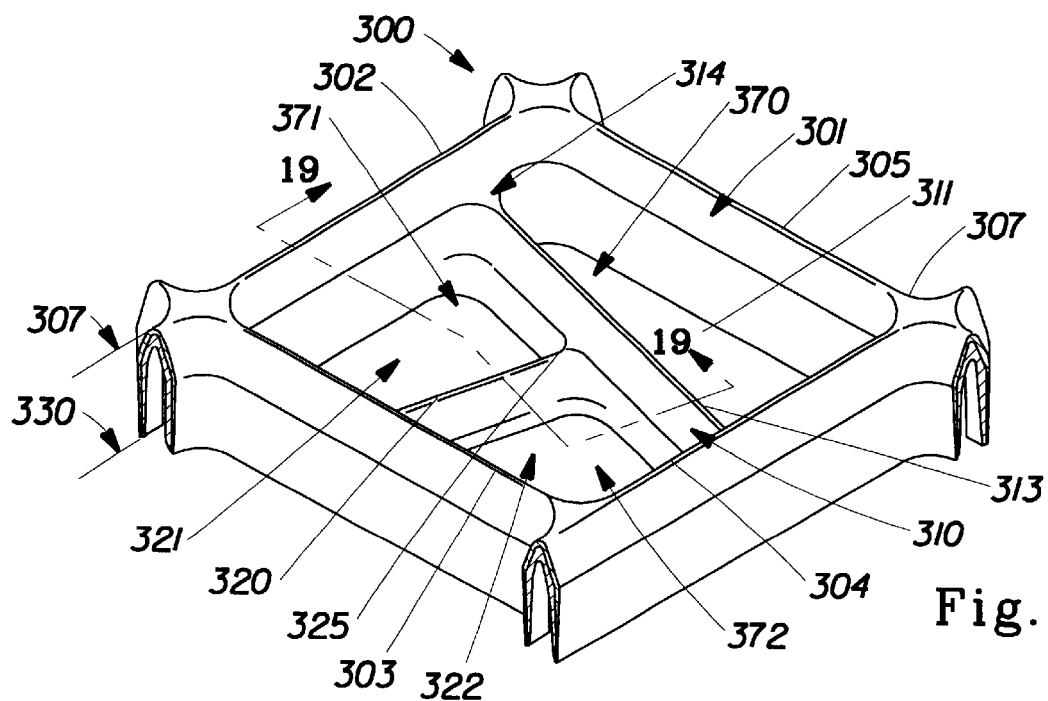
FIG. 18 is an enlarged, partially segmented perspective illustration of an alternative elastomeric web of the present invention.
Figure 19:
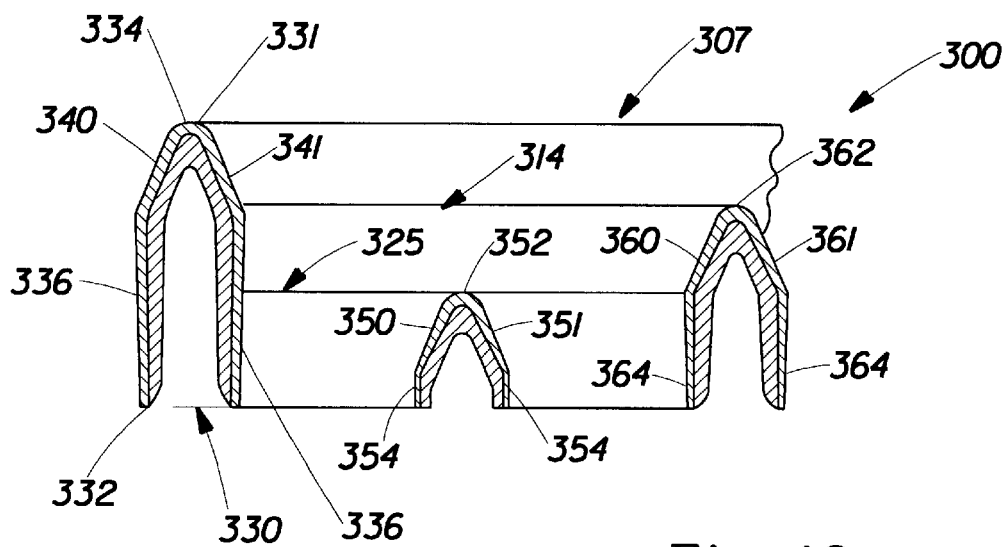
FIG. 19 is an enlarged cross-sectional illustration of the web of FIG. 18 taken along section line 19—19.

While the web embodiment generally disclosed in FIG. 2 represents a particularly preferred embodiment of the present invention, any number of interconnecting members may be employed within web structures of the present invention, e.g., secondary, tertiary, etc. An example of such a structure is shown in FIG. 18 which also shows a variant of upwardly concave-shaped cross-sections of interconnecting members. The aperture network shown in FIG. 18 comprises a primary aperture 301 formed by a multiplicity of primary interconnecting elements, e.g., elements 302, 303, 304 and 305 interconnected to one another in uppermost plane 307 of the web 300, said opening being further subdivided into smaller secondary apertures 310 and 311 by secondary interconnecting member 313 at an intermediate plane 314. Primary aperture 310 is further subdivided by tertiary interconnecting member 320 into even smaller secondary apertures 321 and 322, respectively, at a still lower plane 325 within web 300. As can be seen from FIG. 19, which is taken along section line 19—19 of FIG. 18, planes 314 and 325 are generally parallel to and located intermediate uppermost plane 307 and lowermost plane 330.

In the web embodiment illustrated in FIGS. 17 and 18, the primary and secondary interconnecting members are further connected to intersecting tertiary interconnecting members, e.g., tertiary interconnecting members 320, which also exhibit a generally upwardly concave-shaped cross-section along their length. The intersecting primary, secondary and tertiary interconnecting members terminate substantially concurrently with one another in the plane 330 of the second surface 332 to form a multiplicity of openings or apertures in the web's second surface, e.g., apertures 370, 371 and 372. It is clear that the interconnected primary, secondary and tertiary interconnecting members located between the first and second surfaces of the web 300 form a closed network connecting each of the primary apertures, e.g., aperture 301 in the first surface 331 of the web, with a multiplicity of secondary apertures, e.g., apertures 370, 371 and 372, in the second surface 332 of the web.

As will be appreciated, the generally upwardly concave-shaped interconnecting members utilized in webs of the present invention may be substantially straight along their entire length. Alternatively, they may be curvilinear, they may comprise two or more substantially straight segments or they may be otherwise oriented in any desired direction along any portion of their length. There is no requirement that the interconnecting members be identical to one another. Furthermore, the aforementioned shapes may be combined in any desired fashion to produce whatever pattern is desired. Regardless of the shape ultimately selected, the upwardly concave-shaped cross-section which exists along the respective lengths of the interconnected interconnecting members helps impart resilience to elastomeric webs of the present invention, as well as three-dimensional stand-off.

It will be obvious to those skilled in the art that various changes and modifications can be made without departing from the spirit and scope of the present invention. For example, in the event it is desired to produce webs of the present invention wherein a predetermined portion of the web is capable of preventing fluid transmission, it is feasible to perform the debossing operation without causing rupture of the web in its second surface. Commonly assigned U.S. Pat. No. 4,395,215 issued to Bishop on Jul. 26, 1983 and commonly assigned U.S. Pat No. 4,747,991 issued to Bishop on May 31, 1988, each of which are hereby incorporated herein by reference, fully disclose how to construct tubular forming structures which are capable of producing three-dimensionally expanded films which are uniformly debossed, but apertured only in predetermined areas.

It is believed that the description contained herein will enable one skilled in the art to practice the present invention in many and varied forms. Nonetheless, the following exemplary embodiment and analytical method is set forth for the purpose of illustrating the beneficial elastic reliability of a particularly preferred elastomeric web of the present invention.

EXAMPLE

A planar coextruded multilayer film was produced and then formed by methods disclosed above into an elastomeric web of the present invention, generally as shown in the photomicrographs of FIGS. 9–11. The coextruded film comprised three layers as depicted in FIG. 4, with the elastomeric layer comprising styrenic triblock copolymer and the skin layers comprising polyolefinic material. The total gauge of the film was approximately 0.09 mm (3.5 mils) with the elastomeric layer being approximately 75–90% of the thickness prior to forming into a three-dimensional elastomeric web. While being difficult to measure accurately, the gauge of the three-dimensional elastomeric web from the first surface to the second surface was on the order of 1 mm, for a draw ratio of approximately 10:1. In an as-formed, unextended configuration the continuous first surface generally formed a regular pattern of 1 mm square fluid-permeable apertures spaced about 1 mm apart on all sides. The secondary apertures were slightly smaller than the primary apertures giving the elastomeric web an open apertured area of approximately 12–16%.

The exemplary elastomeric web of the present invention exhibited reliable elastic performance by repeated and sustained web strains of up to about 400% or more without significant affect on web elasticity or porosity. In general, the web exhibited a higher modulus in the first extension as the skin layers experienced inelastic strain. Thereafter it is believed that microscopic rugosities formed on the interconnecting members in the regions of inelastic skin layer strain, which resulted in a lower and generally constant web modulus.

In a particularly preferred method of characterizing the desirable elastic behavior of the exemplary elastomeric web a notched tensile test by the analytical method below was used to determine work to break characteristics. Work to break is essentially the area under the stress-strain curve produced while straining from zero strain to break. This analytical method, as outlined below, was chosen to be especially useful in understanding the notch sensitivity of the exemplary elastomeric web and its ability to resist catastrophic failure due to notch propagation during extension. Exemplary elastomeric web samples of the present invention required greater than 40 Kg-mm average work to break. By way of example, when samples of the unapertured planar coextruded film used to form the exemplary three-dimensional web were tested by the same analytical method, they required only about 8 Kg-mm average work to break.

Analytical Methods

The following is a representative analytical method which has been found suitable for determining the performance of porous elastomeric webs in accordance with the present invention.

Notched Tensile Test

This test method is based on ASTM D882-83 and measures the work-to-break characteristic of notched, apertured films or webs. The method is applicable to a wide range of polymer films, webs, and composite structures.

Hardware Components

Electronic tensile tester: A tensile tester with a calibrated universal constant rate of tensile elongation and data collection capability is required. The tester must be equipped with a suitable load cell to measure tensile loading within 25% to 75% of the capacity of the load cell and facilitate data collection. The tester must be equipped with gripping jaws designed for web testing so that web failure in testing occurs within the web and not at the point of gripping. Suitable equipment is well known in the art, and may be obtained from Instron Engineering Corp., Canton Mass., or SINTECH-MTS Systems Corp., Eden Prairie, Minn.

Software Components

Work-to-break calculation: Software for computation of work to break may be utilized. The software calculates the area under the stress/strain curve output of the tensile tester, and may be accomplished in various ways known in the art. For example, the value for work-to-break may be calculated by integrating over the stress/strain curve produced by the tensile tester. In the alternative, the work-to-break may be manually calculated in any of many ways known in the art for finding the area under a geometric curve.

Preparation of Instrumentation and Test Sample

Crosshead speed: 20 inches/minute.

Gauge length: Samples of web material are prepared in strips one inch wide, with a gauge length of 2 inches.

Notching: Each sample of web material is notched with a new razor blade by making a one-half inch long transverse slit across the apertures near the middle of the gauge length.

Procedure: The notched web sample is inserted into the jaws of the calibrated tensile tester and loaded so to eliminate any slack in the sample. The notched sample is then pulled to failure while the data collection devices record the stress/strain data and the work-to-break calculations are accomplished.

What is claimed is:

1. A porous, macroscopically-expanded, three-dimensional elastomeric web having a continuous first surface and a discontinuous second surface, said first surface and said second surface being located in substantially parallel planes which are remote from one another, said elastomeric web comprising a multiplicity of elastomeric interconnecting members of upwardly concave-shaped cross-section for substantially decoupling applied strain-induced stresses in said first surface from said second surface, said interconnecting members defining at least one primary aperture in said first surface, said primary aperture having a major axis and a minor axis perpendicular to said major axis, said major axis oriented generally orthogonal to said applied strain-induced stresses, said major axis has a first length and said minor axis has a second length which is less than said first length of said major axis when said web is unstrained and having an aspect ratio of said first length of said major axis to said second length of said minor axis of greater than about 5:1 when said web is untensioned, said interconnected sidewall portions extending in the direction of said second surface, and terminating to form at least one secondary aperture having tear initiation sites in said second surface of said elastomeric web, such that strain-induced stresses on said elastomeric web are substantially decoupled from tear initiation sites in said secondary apertures, at least until said second surface is no longer remote from said plane of said first surface when said stresses are applied to said web.

2. The elastomeric web of claim 1, wherein said elastomeric web comprises a formed film, said formed film comprising at least one substantially elastomeric layer having a first side and a second side and at least one substantially less elastomeric skin layer substantially continuously joined to one side of said substantially elastomeric layer prior to the application of said stresses to said web.

3. The elastomeric web of claim 1, wherein said elastomeric web comprises a formed film, said formed film comprising at least one substantially elastomeric layer having a first side and a second side, said elastomeric layer being disposed between two substantially less elastomeric skin layers, each of said skin layers substantially continuously joined to one of said sides of said substantially elastomeric layer prior to the application of said stresses to said web.

4. The elastomeric web of claim 1, comprising at least one intermediate interconnecting member in a plane intermediate said first and second surfaces, whereby at least one of said primary apertures in said first surface of said web is in fluid communication with at least two secondary apertures in said second surface of said web.

5. The elastomeric web of claim 1, wherein said web is elastomeric at strains up to 400%.

6. The elastomeric web of claim 1, wherein said web exhibits greater than 40 kg-mm work to break in a notched tensile test.

7. The elastomeric web of claim 1, further comprising a fibrous nonwoven material bonded to at least one side of said elastomeric web, such that said elastomeric web and said nonwoven material form a composite laminate.

8. A disposable absorbent article, comprising said porous, macroscopically-expanded, three-dimensional elastomeric web of claim 1.

9. A macroscopically-expanded, three-dimensional, elastomeric web having a continuous first surface and a discontinuous second surface remote from said first surface, said elastomeric web comprising:
  (a) a multilayer formed film comprising at least one substantially elastomeric layer having a first side and a second side and at least one substantially less elastomeric skin layer substantially continuously joined to one side of said substantially elastomeric layer prior to the application of stress to said web, said substantially elastomeric layer comprises a hydrogenated poly styrene-isoprene/butadiene-styrene; and
  (b) interconnecting members originating substantially concurrently in said first surface as a continuous network defining a plurality of primary apertures, each of said primary apertures having a major axis and a minor axis perpendicular to said major axis, said major axis generally orthogonal to said applied strain-induced stresses, said interconnecting members terminating substantially concurrently in said second surface as a plurality of secondary apertures, said secondary apertures having tear initiation sites in said second surface of said elastomeric web, such that strain-induced stresses on said elastomeric web are substantially decoupled from tear initiation sites in said secondary apertures, at least until said second surface is no longer remote from said plane of said first surface when said stresses are applied to said web, each of said primary apertures being in fluid communication with at least one secondary aperture.

10. The elastomeric web of claim 9, wherein said multilayer formed film comprises at least one substantially elastomeric layer having a first side and a second side, said elastomeric layer being disposed between two substantially less elastomeric skin layers, each of said skin layers substantially continuously joined to one of said sides of said substantially elastomeric layer prior to the application of stress to said web.

11. The elastomeric web of claim 9, wherein said web is elastomeric at strains up to about 400%.

12. The elastomeric web of claim 9, wherein said web exhibits greater than 40 kg-mm work to break in a notched tensile test.

13. The elastomeric web of claim 9, further comprising a fibrous nonwoven material bonded to at least one side of said elastomeric web, such that said elastomeric web and said nonwoven material form a composite laminate.

14. A disposable absorbent article, comprising said macroscopically-expanded, three-dimensional elastomeric web of claim 9.

15. A macroscopically-expanded, three-dimensional, elastomeric web having a continuous first surface and a discontinuous second surface remote from said first surface, said elastomeric web comprising:
  (a) a multilayer formed film comprising at least one substantially elastomeric layer having a first side and a second side and at least one substantially less elastomeric skin layer substantially continuously joined to one side of said substantially elastomeric layer prior to the application of stress to said web; and
  (b) interconnecting members originating substantially concurrently in said first surface as a continuous network defining a plurality of primary apertures, each of said primary apertures having a major axis and a minor axis perpendicular to said major axis, said major axis generally orthogonal to said applied strain-induced stresses, said major axis has a first length and said minor axis has a second length which is less than said first length of said major axis when said web is unstrained and having an aspect ratio of said first length of said major axis to said second length of said minor axis of greater than about 5:1 when said web is untensioned, said interconnecting members terminating substantially concurrently in said second surface as a plurality of secondary apertures, said secondary apertures having tear initiation sites in said second surface of said elastomeric web, such that strain-induced stresses on said elastomeric web are substantially decoupled from tear initiation sites in said secondary apertures, at least until said second surface is no longer remote from said plane of said first surface when said stresses are applied to said web, each of said primary apertures being in fluid communication with at least one secondary aperture.

16. A disposable absorbent article, comprising said macroscopically-expanded, three-dimensional elastomeric web of claim 15.

* * * * *

UNITED STATES PATENT AND TRADEMARK OFFICE
CERTIFICATE OF CORRECTION

PATENT NO. : 6,452,063 B1
DATED : September 17, 2002
INVENTOR(S) : John Joseph Curro et al.

It is certified that error appears in the above-identified patent and that said Letters Patent is hereby corrected as shown below:

<u>Title page,</u>
Item [57], ABSTRACT,
Line 9, delete "front" and insert -- from --.

Signed and Sealed this

Third Day of January, 2006

JON W. DUDAS
*Director of the United States Patent and Trademark Office*